United States Patent [19]
Gjerset

[11] Patent Number: 6,054,467
[45] Date of Patent: *Apr. 25, 2000

[54] DOWN-REGULATION OF DNA REPAIR TO ENHANCE SENSITIVITY TO P53-MEDIATED APOPTOSIS

[75] Inventor: Ruth A. Gjerset, San Diego, Calif.

[73] Assignee: Sidney Kimmel Cancer Center, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/675,887

[22] Filed: Jul. 5, 1996

[51] Int. Cl.$^7$ .......................... A01N 43/42; A01N 37/18; A61K 31/47; A61K 31/165

[52] U.S. Cl. .......................... 514/309; 514/617; 514/619; 514/456; 435/7.1; 435/7.23

[58] Field of Search ..................... 435/7.1, 7.23; 436/63; 514/309, 617, 619, 456

[56] References Cited

U.S. PATENT DOCUMENTS

| | | | |
|---|---|---|---|
| 5,527,676 | 6/1996 | Vogelstein et al. | 435/6 |
| 5,532,220 | 7/1996 | Lee et al. | 514/44 |

FOREIGN PATENT DOCUMENTS

| | | |
|---|---|---|
| 0 39 323 A2 | 10/1990 | European Pat. Off. . |
| WO 90/05180 | 5/1990 | WIPO . |
| WO 91/15580 | 10/1991 | WIPO . |
| WO 94/18992 | 9/1994 | WIPO . |
| WO 94/24297 | 10/1994 | WIPO . |
| WO 95/14101 | 5/1995 | WIPO . |
| WO 95/14102 | 5/1995 | WIPO . |
| WO 95/23867 | 9/1995 | WIPO . |

OTHER PUBLICATIONS

Gura. "Systems for identifying new drugs are often faulty" Science. vol. 278. pp. 1041–1042, Nov. 7, 1997.

Dermer. "Another Anniversary for the war on Cancer" Bio/Technology. vol. 12, p. 320, Mar. 12, 1994.

Wang et al "The XPB and XPD DNA helicases are components of the p53–mediated apoptosis pathway" Genes and Dev. vol. 10 pp. 1219–1232, May 15, 1996.

Li et al, "Induction of apoptosis by b–lapachone in human prostate cancer cells" Cancer Res. vol. 55 No. 17, pp. 3712–3715, Sep. 1, 1995.

Del Bino et al, "Apoptotic cell death triggered by camptothecin or teniposide. The cell cycel specificity and effects of ionizing radiation" Cell Prolif. vol. 25, pp. 537–548, 1992.

Gotz et al, "p53: DNA damage, DNA repair, and apoptosis" Rev. Physiol. Biochem. Pharmacol. vol. 127, pp. 65–85, 1995.

Mi et al., "Base Excision Repari of 5–Hydroxymethyl–2'–Deoxyuridine (HMDURD) from DNA Induces High Molecular Weight DNA Double Strand Breaks and Apoptosis in Mammalian Fibroblasts Containing Mutant "P53, Proceed. Amer. Assoc. Cancer. Res., abstract 169, 37:24, Mar. 1996.

Venkatachalam et al., Modulation of DNA Damage Induced P53 Response in Human Cells, Proceed. of the Amer. Assoc. Cancer Res., abstract 951, 37:137, 1996.

Stierum et al., "Inhibition of Poly(ADP–Ribose) Polymerase Increases (+–)–Anti–Benzo (A) Pyrene Diolepoxide–Induced Micronuclei Formation and P53 Accumulation in Isolated Human Peripheral Blood Lymphocytes," Carcinogenesis, 16(11):2765–2771, 1995.

Fanjul et al., "A New Class of Retionoids With Selective Inhibition of AP–1 Inhibits Proliferation", Nature, 372(6501):107–111, 1994.

In: Dictionary of Natural Compounds, Volume One, Chapman and Hall, London, 1151, Entry C–01948, 1994.

In: Dictionary of Natural Compounds, Volume One, Chapman and Hall, London, 1151, Entry N–00835, 1994.

Lane, "P53, Guardian of the Genome," Nature, 358:15–16, 1992.

Rauchuang Ding et al., "Depletion of Poly(ADP–Ribose) Polymerase by Antisense RNA Expression Results in a Delay in DNA Strand Break Rejoining," J. Biol. Chem., 267(18):12804–12812, 1992.

International Search Report, NOv. 14, 1997 (INGN:032P—).

Adler et al., "UV Irradiation and Heat Shock Mediate JNK Activation via Alternate Pathways," Journal of Biological Chemistry, 270(44):26071–26077, 1995.

Ali–Osman et al., "Enhanced repair of a Cisplatin–Damaged Reporter Chloramphenicol–O–Acetyltransferase Gene and Altered Activities of DNA Polymerases $\alpha$ and $\beta$, and DNA Ligase in Cells of a Human Malignant Glioma Following In Vivo Cisplatin Therapy," Journal of Cellular Biochemistry, 54:11–19, 1994.

Baker et al., "Chromosome 17 Deletions and p53 Gene Mutations in Coloractal Carcinomas," Science, 244:217–221, Apr. 1989.

Baker et al., "p53 Gene Mutations Occur in Combination with 17p Allelic Deletions as Late Events in Colorectal tumorigenesis," Cancer Research, 50:7717–7722, Dec. 1990.

Baker et al., "Suppression of Human Colorectal Carcinoma Cell Growth by Wild–Type p53," Science, 249:912–915, 1990.

Baverstock and Will, "Evidence for the dominance of direct excitaiton of DNA in the formation of strand breaks in cells following irradiation," International Journal of Radiation Biology, 55(4): 563–568, 1989.

(List continued on next page.)

Primary Examiner—Yvonne Eyler
Attorney, Agent, or Firm—Arnold, White & Durkee

[57] ABSTRACT

The present invention details methods for the treatment of cancer. In particular it concerns the induction of apoptosis in cancer cells following treatment with inhibitors of DNA repair in combination with p53. Treatment of glioblastoma and breast tumor cells with inhibitors of DNA repair induced growth suppression that was a result of p53-mediated apoptosis. Thus it appears that inhibitors of DNA repair in combination with p53 is involved in restoration of p53-mediated apoptosis.

19 Claims, 11 Drawing Sheets

OTHER PUBLICATIONS

Bigner et al., "Cytogenetics of Human Brain Tumors," *Cancer Genetic Cytogenetics*, 47: 141–154, 1990.

Bigner et al., "Heterogenetity of Genotypic and Phenotypic Characteristics of Fifteen Permanent Cell Lines Derived from Human Gliomas," *Journal of Neuropathology and Experimental Neurology*, 40(3): 201–229, 1981.

Carter et al., "Adenovirus Containing a Deletion of the Early Region 2A Gene Allows Growth of Adeno–Associated Virus with Decreased Efficiency," *Virology*, 191:473–476, 1992.

Clarke et al., "Thymocyte apoptosis induced by p53–dependent and independent pathways," *Nature*, 362: 849–852, 1993.

Davidson et al., "A Model System for In Vivo Gene Transfer into the Central Nervous System Using an Adenoviral Vector," *Nature Genetics*, 3:219–223, Mar. 1993.

DiLeonardo et al., "DNA damage triggers a prolonged p53–dependent $G_1$ arrest and long–term induction of Cip 1 in normal human fibroblasts," *Genes and Development*, 8: 2540–2551, 1994.

Diller et al., "p53 Functions as a Cell Cycle Control Protein is Osteosarcomas," *Molecular and Cellular Biology*, 10(11):57721–5781, Nov. 1990.

Donehower et al., "Deficiency of p53 accelerates mammary tumorigenesis in Wnt–1 transgenic mice and promotes chromosomal instability," *Genes and Development*, 9: 882–895, 1995.

El–Deiry et al., "WAF1CIP1 Is Induced in p53–mediated $G_1$ Arrest and Apoptosis," *Cancer Research*, 54: 1169–1174, 1994.

El–Diery et al., "WAF1, a Potential Mediator of p53 Tumor Suppression," *Cell*, 75: 817–825, 1993.

Eliyahu et al., "Meth A Fibrosarcoma Cells Express Two Transforming Mutant p53 Species," *Oncogene*, 3:313–321, 1988.

Eliyahu et al., "p53 — A Potential Suppressor Gene?" *Journal of Cellular Biochemistry*, UCLA Symposia on Molecular & Cellular Biology, Abstracts, 19th Annual Meeting, Supplement 14C:264, Abstract No. I 030, Feb. 3–Mar. 11, 1990.

Eliyahu et al., "Wild–Type p53 Can Inhibit Oncogene–Mediated Focus Formation," *Proc. Natl. Acad. Sci. USA*, 86:8763–8767, Nov. 1989.

Evans et al., "Differential Sensitivity to the Induction of Apoptosis by Cisplatin in Proliferating and Quiescent Immature Rat Thymocytes Is Independent of the Levels of Drug Accumulation and DNA Adduct Formation," *Cancer Research*, 54: 1596–1603, 1994.

Fanjul et al., "A new class of retinoids with selective inhibition of AP–1 inhibits proliferation" *Nature*, 372: 107–111, 1994.

Finlay et al., "The p53 Proto–Oncogene Can Act as a Suppresor of Transformation," *Cell*, 1083–1093, Jun. 1989.

Fraval et al., "Increased Sensitivity of UV–Repair–Deficient Human Cells to DNA Bound Platinum Products Which Unlike Thymine Dimers Are Not Recognized by an Endomuclease Extracted From *Micrococcus Luteus*," *Mutation Research*, 51: 121–132, 1978.

Fujiwara et al., "Induction of Chemosensitivity in Human Lung Cancer Cells In Vivo by Adenovirus–mediated Transfer of the Wild–Type p53 Gene," *Cancer Research*, 54: 2287–2291, 1994.

Gebhardt et al., "A Tumor Suppressor Proto–Oncogene p53 Can Block Progression Through the Cell Cycle," Association of American Physicians, American Society for Clinical Investigation, American Federation for Clinical Research, Subspecialty Meetings, Sheraton Washington Hogel, Washington, D.C., May 6, 1990, Abstract.

Gipp et al., "DNA Damage Induced in HT–29 Colon Cancer Cells by Exposure to 1–Methyl–2–Nitrosoimidazole, A Reductive Metabolite of 1–Methyl–2–Nitroimidazole," *Biochemical Pharmacology*, 42 (Suppl): S127–S133, 1992.

Gjerset et al., "Use of Wild–Type p53 to Achieve Complete Treatment Sensitization of Tumor ells Expressing Endogenous Mutant p53," *Molecular Carcinogenesis*, 14:275–285, 1995.

Graham and Prevec, "Manipulation of Adenovirus Vectors," *Methods in Molecular Biology, Gene Transfer and Expression Protocols*, E.J. Murray (ed.), The Humana Press, Inc., vol. 7, Chapter 11, pp. 109–128, 1991.

Hinds et al., "Mutation is Required to Activate the p53 Gene for Cooperation with the ras Oncogene and Transformation," *Journal of Virology*, 63(2):739–746, Feb. 1989.

Hinds et al., "The p53 Proto–Oncogene Can Suppress Transformation by Other Oncogenes, and Mutations in the Proto–Oncogene Can Activate the Gene Transformation," *Common Mechanisms of Transformation by Small DNA Tumor Viruses*, Chapter 7, pp. 83–101, 1989.

Hinds, "Biological Consequences of Mutation of the p53 Proto–Oncogene," *UMI Dissertation Services*, Oct. 1989.

Huang et al., "Suppression of the Neoplastic Phenotype by Replacement of the RB Gene in Human Cancer Cells," *Science*, 242–1563–1566, Dec. 1988.

Izumoto et al., "Homozygous deletions of $p16^{INK4A}$/MTS1 and $p15^{INK4B}$MTS2 genes in glioma cells and primary glioma tissues," *Cancer Letters*, 97: 241–247, 1995.

Jen et al., "Deletion of p16 and p15 Genes in Brain Tumors," *Cancer Research*, 54: 6353–6358, 1994.

Kaden et al., "High frequency of large spontaneous deletions of DNA in tumor–derived CHEF cells." Proceedings of the National Academy of Science USA, 86: 2306–2310, 1989.

Kamb, Alexander, "Cell–Cycle Regulators and Cancer," *Trends in Genetics*, 11(4): 136–140, 1995.

Kashani–Sabet et al., "Cyclosporin A Suppresses Ciplatin–induced c–fos Gene Expression in Ovarian Carcinoma Cells," *Journal of Biological Chemistry*, 265(19): 11285–11288, 1990.

Kashani–Sabet et al., "Differential Oncogene Amplification in Tumor Cells from a Patient Treated with Cisplatin and 5–Fluorouracil," *European Journal of Cancer*, 26(3): 383–390, 1990.

Kimler, "The 9L Rat Brain Tumor Model for Pre–Clinical Investigation of Radiation–chemotherapy Interactions," *Journal of Neuro–ONcology*, 20:103–109, 1994.

Klessig et al., "Introduction, Stable Integration, and Controlled Expression of a Chimeric Adenovirus Gene Whose Product is Toxic to the Recipient Human Cell," *Molecular and Cellular Biology*, 4(7):1354–1362, Jul. 1984.

Lamb and Crawford, "Characterization of the Human p53 Gene," *Molecular and Cellular Biology*, 6(5):1379–1385, May 1986.

Lane, D.P. "p53, guardian of the genome," *Nature*, 358: 15–16, 1992.

Lee et al., "Molecular Basis of Tumor Suppression by the Human Retinoblastoma Gene," *Journal of Cellular Biochemistry*, UCLA Symposia on Molecular & Cellular Biology, Abstracts, 19th Annual Meeting, Supplement 14C, Abstract No. I 001, Feb. 3–Mar. 11, 1990.

Levine et al., "The p53 Growth Suppressing Gene Can Inhibit Transformation by Other Oncogenes," *The Journal of Cell Biology*, The American Society for Cell Biology, Twenty–ninth Annual Meeting, Nov. 5–9, 1989, Houston, Texas, Abstracts, 1989.

Levine et al., "The p53 Growth Suppressor Gene," *Journal of Biochemistry*, UCLA Symposia on Molecular & Cellular Biology, Abstracts, 19th Annual Meeting, Supplement 14C:264, Abstract No. I 029, Feb. 3 – Mar. 11, 1990.

Liu and Miller, "Eukaryotic DNA Topoisomerases: Two Forms of Type I DNA Topoisomerases from HeLa Cell Nuclei," *Proc Natl Acad Sci USA*, 48(6):3487–3491, Jun. 1981.

Liu et al., "Cleavage of DNA by Mammalian DNA Topoisomerase II," *Journal of Biological Chemistry*, 258(24): 15365–15370, 1983.

Lotem and Sachs, "Hematopoietic Cells From Mice Deficient in Wild–Type p53 Are More Resistant to Induction of Apoptosis by Some Agents," *Blood*, 82(4): 1092–1096, 1993.

Lowe et al., "p53 Status and the Efficacy of Cancer Therapy In Vivo," *Science*, 266: 807–810, 1994.

Lowe et al., "p53–Dependent Apoptosis Modulates the Cytotoxicity of Anticancer Agents," *Cell*, 74: 957–967, 1993.

Lukas et al., "Retinoblastoma–protein–dependent cell–cycle inhibition by the tumour suppressor p16," *Nature*, 375: 503–506, 1995.

Malkin et al., "Mutant ⎯Confers Tumorignicity to a Cell Line Lacking p53: Evidence for a Second p53 Function in Tumor Formation," *Blood*, 76(10, Suppl. 1):238a, 1990.

Mercer et al., "Antiproliferative Effects of Wild Type Human P53," *Journal of Cellular Biochemistry*, UCLA Symposia on Molecular & Cellular Biology, Abstracts, 19th Annual Meeting, Supplement 14C:264, Abstract No. I 224, Feb. 3–Mar. 11, 1990.

Mercer et al., "Negative growth regulation in a glioblastoma tumor cell line that conditionally expresses human wild–type p53," Proceedings of the National Academy of Science USA, 87: 6166–6170, 1990.

Minna et al., "The Molecular Pathogenesis of Lung Cancer Involves the Accumulation of a Large Number of Mutations in Dominant Oncogenes and Multiple Tumor SUppressor Genes (Recessive Oncogenes)," *Journal of Cellular Biochemistry*, UCLA Symposia on Molecular & Cellular Biology, Abstracts, 19th Annual Meeting, Supplement 14C:264, Abstract No. I 003, Feb. 3 – Mar. 11, 1990.

Miyashita et al., "Tumor suppressor p53 is a regulator of bcl–2 and bax gene expression in vitro and in vivo," *Oncogene* 9: 1799–1805, 1994.

Moulton et al., "MTS1/p16/CDKN2 Lesions in Primary Glioblastoma Multiforme," *American Journal of Pathology*, 146(3): 613–619, 1995.

Moynihan et al., "The Role of Chemotherapy in the Treatment of Primary Tumors of the Central Nervous System," *Cancer Investigation*, 12(1): 88–97, 1994.

Nigro et al., "Mutations inthe p53 gene occur in diverse human tumour types," *Nature*, 342: 705–708, 1989.

Nishikawa et al., "Loss of P16$^{INK4}$ Expression is Frequent in High Grade Gliomas," *Cancer Research*, 55: 1941–1945, 1995.

Noble et al., "Effects of Exogenous Wild–Type p53 on a Human Lung Carcinoma Cell Line with Endogenous Wild–Type p53," *Experimental cell Research*, 203: 297–304, 1992.

Oshita and Saijo, "Rapid Polymerase Chain Reaction Assay to Detect Variation in the Extent of Gene–Specific Damage Between Cisplatin– or VP–16–Resistant and Sensitive Lung Cancer Cell Lines," *Jpn. J. Cancer Res.*, 85:669–673, Jul. 1994.

Rogel et al., "p53 Cellular Tumor Antigen: Analysis of mRNA Levels in Normal Adult Tissues, Embryos, and Tumors," *Molecular and Cellular Biology*, 5(10): 2851–2855, 1985.

Sager, "Tumor Suppressor Genes: The Puzzle and the Promise," *Science*, 246:1406–1412, Dec. 1989.

Scanlon et al., "Overexpression of DNA Replication and Repair Enzymes in Cisplatin–Resistant Human Colon Carcinoma HCT8 Cells and Circumvention by Azidothymidine," *Cancer Communications*, 1(4):269–275, 1989.

Scanlon et al., "Cisplatin Resistance in Human Cancers," *Pharmaceutical Therapy*, 52: 385–406, 1991.

Scanlon et al., "Molecular Basis of Cisplatin Resistance in Human Carcinomas: Model Systems and Patients," *Anticancer Research*, 9:1301–1312, 1989.

Shaw et al., "Induction of apoptosis by wild–type p53 in a human colon tumor–derived cell line," Proceedings of the National Academy of Science USA, 89: 4495–4499, 1992.

Tlsty, Thea D., "Normal diploid human and rodent cells lack a detectable frequency of gene amplification," Proceedings of the National Academy of Science USA, 87: 3132–3136, 1990.

Van Meir et al., "Release for an Inhibitor of Angiogenesis Upon Induction of Wild Type p53 Expression in Glioblastoma Cells," *Nature Genetics*, 8:171–176, Oct. 1994.

Vincent et al., "Gene Therapy for Malignant Brain Tumors," *Cancer Gene Therapy*, 1(4):328, Abstract No. V–80, San Diego, California, Nov. 10–12, 1994.

Vogelstein et al., "Genetic Alterations Accumulate During Colorectal Tumorigenesis," Negative Controls on Cell Growth, *Journal of Cellular Biochemistry*, USLA SYmposia on Molecular and Cellular Biology, 19th Annual Meetings, Feb. 3–Mar. 11, 1990, Abstract #I004, Supplement 14C, 1990.

Wahl et al., "Loss of normal p53 function confers sensitization to Taxol by increasing G2/M arrest and apoptosis," *Nature Medicine*, 2(1): 72–79, 1996.

Wu and Levine, "p53 and E2F–1 Cooperate to Mediate Apoptosis," *Proc Natl Acad Sci USA*, 91:3602–3606, Apr. 1994.

Yonish–Rouach et al., "Wild–type p53 induces apoptosis of myeloid leukaemic cells that is inhibited by interleukin–6," *Nature*, 352: 345–347, 1991.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:1:

TGGGATTACA CGTGTGAACC AACC      24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:2:

GATCCACAGT CTGCCTGAGT CACT      24

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:3:

CCTAGAAAGC ACATGGAGAG CTAG      24

DOWN-REGULATION OF DNA REPAIR TO ENHANCE SENSITIVITY TO P53-MEDIATED APOPTOSIS

BACKGROUND OF THE INVENTION

1. Field of the Invention

The present invention relates generally to the field of cancer therapy. More particularly, it concerns a method of inducing p53-mediated apoptosis in tumor cells by inhibiting DNA repair.

2. Description of Related Art

Normal tissue homeostasis is achieved by an intricate balance between the rate of cell proliferation and the rate of cell death. Disruption of this balance is thought to be a major event in the development of cancer. The inhibition of apoptosis, or programmed cell death, has been linked to this disruptive event. The effects of cancer are catastrophic, causing over half a million deaths per year in the United States alone.

Though conventional therapies are available, development of resistance to such treatment is a major obstacle to treatment of cancer. For example, glioblastoma multiforme is the most common intracranial brain tumor and is particularly resistant to therapy, and rapidly becomes more resistant as therapy continues. Glioblastoma tumors are highly vascularized, infiltrate the brain extensively and can attain a very large size. Glioblastomas are unilaterally fatal and patients have a mean survival time of about one year from the time of diagnosis.

Traditional treatment modalities for glioblastoma include surgery, radiotherapy, and chemotherapy. However, glioblastomas respond poorly to most chemotherapeutic agents, even though the blood brain barrier is broken down as a consequence of the disease. Certain chemotherapeutic agents such as cisplatin, carmustine, procarbazine and 5-fluororacil are somewhat efficacious in the treatment of glioblastoma but the tumors are never completely eradicated by these methods. A major reason for the failure of traditional treatment therapies of glioblastoma is the development of resistance in subsets of tumor cells. One reason for this resistance appears to be a result of genetic changes that accompany disease progression, including loss of wild-type p53 function. Mutations in p53 occur in over 50% of adult glioblastoma cases and are associated more with disease progression.

The p53 gene is well recognized as a tumor suppressor gene (Montenarh, 1992). There is now considerable evidence linking mutations of p53 in the oncogenesis of many human cancers. There are numerous reports demonstrating that the growth of colon, glioblastoma, breast cancer, osteosarcoma and lung tumor cells can be suppressed by the expression of wild-type p53. The introduction of wild-type p53 into a wide variety of p53-mutated cells, using viral delivery methods, has resulted in the expression of the wild-type p53 transgene and a suppression of the malignant phenotype. These observations demonstrate that a high level of expression of wild-type p53 is a desirable course for the treatment of oncogenic malignancy.

More recently, p53 has been shown to be a trigger of apoptosis (Yonish-Rouacli et al., 1991; Shaw et al., 1992; Lowe et al., 1993; Lotem and Sachs, 1993; Clarke et al., 1993) which suggests that the disruption of p53 in tumors has significant consequences for cancer therapy. The desensitization of tumor cells to the effects of traditional cancer therapies as a result of p53 mutation may aid in the progression of disease. In addition to p53 mutations, cancer therapies such as radiotherapy and chemotherapy that induce DNA damage to a tumor cell contribute to the development of resistance of tumors. Several studies suggest that treatment of tumors with DNA damaging agents results in up-regulated DNA damage repair mechanisms, which could account for increased resistance to DNA damaging therapy. In normal cells, DNA damage results in cell cycle arrest and induction of DNA repair mechanisms, so as to prevent the transfer of damaged DNA to the next generation of cells. Cells that sustain high levels of DNA damage, such as tumor cells that exhibit high levels of karyotypic instability, or cells that are treated with DNA damaging agents, are induced to undergo apoptosis. This switch from either arrest and DNA repair or apoptosis is mediated by p53. These effects, among others, show that there remains a need for improved methods of cancer therapy.

SUMMARY OF THE INVENTION

It is, therefore, a goal of the present invention to provide improved methods for the treatment of cancer. More particularly, it is a goal to provide methods for overcoming or limiting the therapy-inhibiting effects of DNA repair in cancer cells. These methods facilitate the function of the tumor suppressor, p53, in the induction of apoptosis in cells sustain DNA damage.

There is provided, according to the present invention a method for the induction of p53-mediated apoptosis in a cell comprising the step of contacting a cell with at least one inhibitory agent that inhibits DNA repair. This method may further comprise contacting the cell with a first stimulatory agent that increases the level of a tumor suppressor in said cell. The tumor suppressor may be p53, p21 or MSH-2, and preferably is p53. The stimulatory agent may be an expression construct that comprises a tumor suppressor gene under the control of a promoter active in eukaryotic cells. The expression construct may be an adenoviral expression construct. Preferably, the said adenoviral expression construct lacks a portion of at least one gene essential to adenoviral replication, such as the El gene. A preferred promoter is the CMV promoter.

Though any inhibitory agent of DNA repair may be used, the method advantageously employs and said inhibitory agent that inhibits the function of a protein selected from the group consisting of c-jun, c-fos, poly-ADP ribose polymerase, DNA polymerase β, topoisomerase I, d-TMP synthase, hMTII-A, uracil DNA glycosylase, alkyl-N-purine DNA glycosylase, DNA ligase IV, DNA ligase III, Hap-1, Ref-1, poly-ADP ribose polymerase and DNA-dependent protein kinase.

In one embodiment, the inhibitory agent is a non-functional version of an agent involved with DNA repair. For example, a mutant jun protein that competitively inhibits c-jun may be employed. In another embodiment, the inhibitory agent is an antisense construct encoding at least a portion of a gene such as c-jun, c-fos, poly-ADP ribose polymerase, DNA polymerase β, topoisomerase I, d-TMP synthase, hMTII-A, uracil DNA glycosylase, alkyl-N-purine DNA glycosylase, DNA ligase IV, DNA ligase U11, Hap-1, Ref-1, poly-ADP ribose polymerase and DNA-dependent protein kinase. In another embodiment, the inhibitory agent is a retinoid, for example, the synthetic retinoid SR11220. In yet another embodiment, the inhibitory agent is 3-aminobenzamide.

The method may also comprise the step of providing a DNA-damaging agent. Suitable DNA-damaging agents included cisplatin, carboplatin, VP 16, teniposide, daunorubicin, doxorubicin, dactinomycin, mitomycin, plicamycin, bleomycin, procarbazine, nitrosourea, cyclophosphamide, bisulfan, melphalan, chlorambucil, ifosfamide, merchlorehtamine, taxol, taxotere, anthracyclines and ionizing radiation.

Tumor cells such as a lung tumor cell, a prostate tumor cell, a breast tumor cell, a colon tumor cell, a liver tumor cell, a brain tumor cell, a kidney tumor cell, a skin tumor cell and an ovarian tumor cell all are contemplated targets of the method. These tumors may be a squamous cell carcinoma, a non-squamous cell carcinoma, a glioblastoma, a sarcoma, a melanoma, a papilloma, a neuroblastoma and a leukemia cell. The tumors may be treated ex vivo or in a subject, such as a human subject.

Delivery of the inhibitory agent, the stimulatory agent and/or the DNA damaging agent is advantageously via direct intratumoral injection. In a more specific embodiment, the injection comprises continuous perfusion of the tumor.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
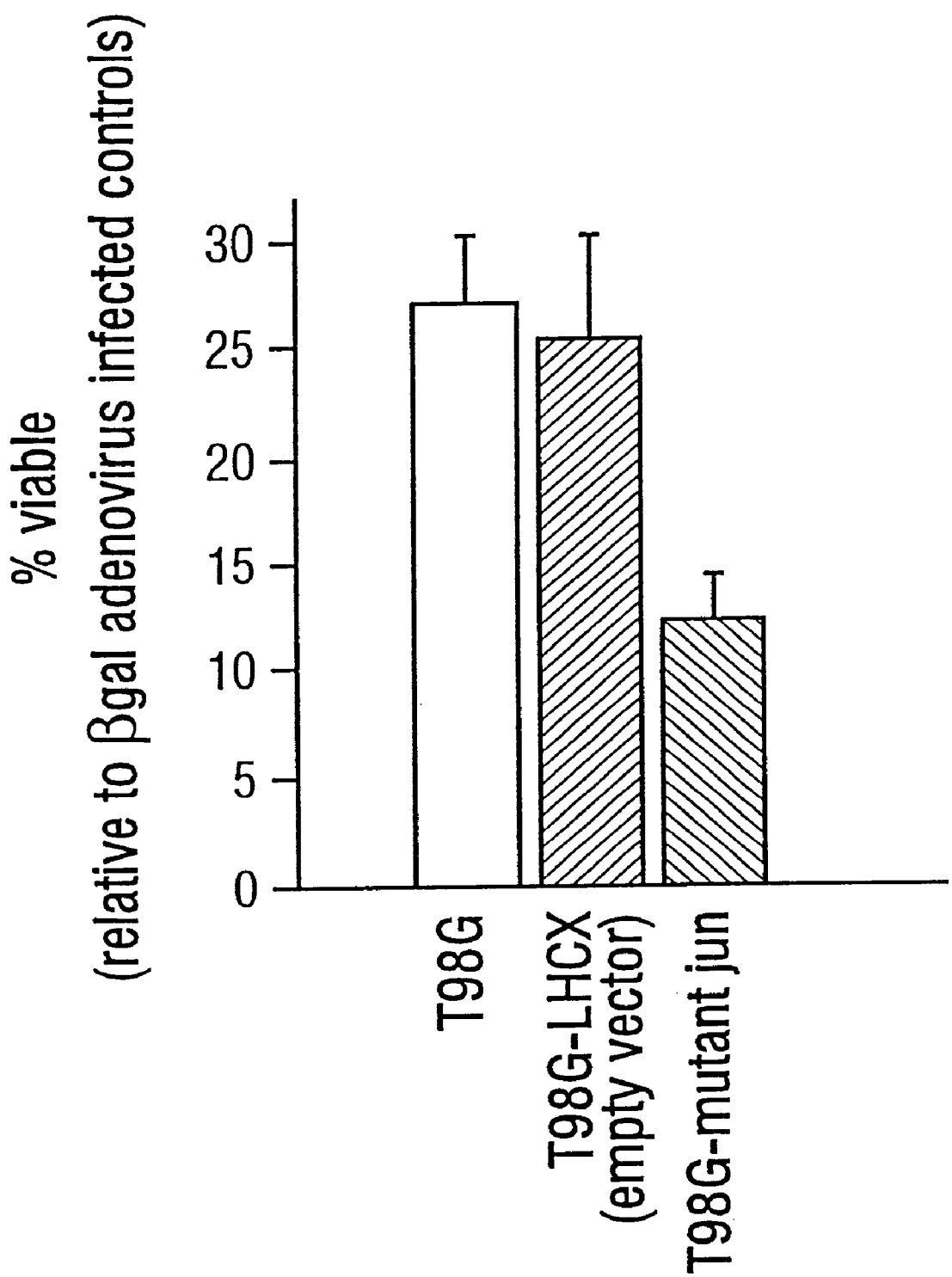
FIG. 1. Cell viability assay. Cell growth was measured after 7 days of untreated parental cells (T98G), parental cells transfected with empty vector (T98GLHCX), and parental cells transfected with a vector expressing mutant jun (T98G-mutant jun) after infection with p53 adenovirus. Percentage viability is relative to the same subclones infected with βgal-adenovirus.

Cancer accounts for the death of over half a million people each year in the United States alone. The causes for cancer are multifactorial, but it is known that aberrations in mechanisms involved with controlled cell death (apoptosis) may result in uncontrolled cell proliferation and, hence, contribute to many cancers. Conventional cancer therapies such as radiotherapy and chemotherapy that result in DNA damage are poorly effective or lose their effectiveness over time in some cancers. A consequence of the treatment of tumor cells with such DNA damaging agents is the induction of DNA repair mechanisms. Up-regulation of DNA repair mechanisms contributes to the increasing resistance of tumors to sustained therapy.

The present invention provides a means of increasing levels of apoptosis in tumor cells through inhibition of DNA damage repair mechanisms. The present invention relies, in part, on the observation that agents that inhibit the expression of DNA repair enzymes sensitize tumor cells to p53-mediated apoptosis. This finding can be employed in a number of ways. First, treatment of tumors which express wild-type p53 with DNA repair inhibitory agents can sensitize the tumors to p53-mediated apoptosis. Second, the delivery of combination therapy, where p53 gene therapy is used in combination with agents that inhibit DNA repair are used to inhibit the DNA repair mechanisms, thereby inducing apoptosis. And third, in a three-part combination therapy, one can deliver a p53 gene, DNA repair inhibitors and DNA damaging agents. Thus, for the purposes of the this application, a "functional" p53 or p53 gene is one that confers this apoptosis-inducing ability on cells. A "wild-type" p53 will accomplish this function. The details of these embodiments of the present invention, as well as others, are described in more detail in the following sections.

A. Role of p53 in Assessing DNA Damage and Therapy Sensitization

In normal cells, DNA damage spontaneously occurs in the form of nucleotide additions, deletions, or substitutions. Upon damage to DNA, the cell cycle is arrested and mechanisms are induced that repair the damaged DNA before completion of the cell cycle and passage of the DNA message to the next generation of cells. Normal expression of wild-type p53 may play a role in determining the end result of DNA damage. WAF1, one of the targets of p53, encodes a $p21^{WAF1/CIP1}$ protein of 21,000 Dalton molecular weight, which is an inhibitor of cyclin-dependent kinase 2 required for the G1-to-S transition (El-Deiry et al., 1993). Low levels of DNA damage may result in p53-mediated induction of this cell cycle inhibitor, which prevents the cell from progressing through the cell cycle and passing on damaged DNA to the next generation. However, DNA damage that is extensive and not easily repaired may preferentially result in the induction of the apoptotic pathway.

Karyotypic instability is a hallmark of cancer and is particularly apparent in glioblastoma (Bigner et al., 1981; Bigner et al., 1990). This instability manifested by an increased level of chromosomal breakage and rearrangement, including translocations, additions, deletions, amplifications, loss of heterozygosity and aneuploidy. Tumor cells show elevated rates of spontaneous gene amplification compared to normal cells, where gene amplification is rarely detected (Tisty, 1990). Spontaneous deletions also occur with increased frequency in tumor cells (Kaden et al., 1989). loss of p53 function, it particular its ability to monitor DNA conditions, may favor the growth of karyotypically unstable cells by removing a trigger for apoptosis that could eliminate cells with unstable genomes (Lane, 1992). Thus, loss of p53 may contribute to the marked aneuploidy and karyotypic instability observed in tumors, for example, glioblastoma.

Genomic instability accompanied by loss of p53-mediated apoptosis also can lead to cancer therapy resistance. Studies of p53 null transgenic mice have shown that normal transgenic hematopoetic cells (Lotem and Sachs, 1993), E1A-expressing transgenic fibroblasts (Lowe et al., 1993) and transformed transgenic fibroblasts (Lowe et al., 1994) were all more resistant to apoptosis following treatment with a variety of anti-cancer agents.

The data presented herein show that glioblastoma cells and other tumor cells lacking functional p53 are significantly more sensitive to the DNA damaging effect of cisplatin and radiation following introduction of am exogenous, wild-type p53 gene. This enhancement of cell death has been shown to be the result of apoptosis. Expression of exogenous wild-type p53 in cells containing an intact normal p53 does not affect the growth of these cells. Since mutation of p53 is widespread in cancer, the use of wild-type p53 as a therapy sensitizer may have far reaching consequences in treating p53-negative associated cancers as well as cancers that contain a functional p53 gene, including but not limited to breast, lung, prostate, colon, liver, brain, skin, ovarian, pancreatic, kidney, lymphoid and renal.

In some cells lacking a functional p53, introduction of exogenous wild-type p53 may achieve only a slowing of growth or reversible growth arrest. Transfer of wild-type p53 into T98G glioblastoma cells slows the growth of the cells but does not induce apoptosis. Similarly, GM47 glioblastoma cells which express an inducible wild-type p53 undergo reversible growth arrest at high levels of p53 induction. However, after de-induction, the cells begin cell cycling (Mercer et al., 1990).

However, because wild-type p53 sensitizes tumor cells to DNA damaging agents, long term expression may not be necessary in certain combined therapies. Transient expression of p53, followed by induction of DNA damage by chemotherapeutic agents of ionizing radiation or other DNA damaging agents, could provide the appropriate trigger to direct the cell into the irreversible apoptotic pathway. Support for this concept has been seen in recent studies involving transient expression of wild-type p53 delivered by an adenovirus that was shown to increase drug sensitivity in culture and induce partial sensitivity when transferred into tumor in vivo (Fugiwara et al., 1994). This phenomenon may further be exploited by use of inhibitors of DNA repair.

Tumor suppression and therapy sensitization through p53 appears to be selective for tumors cells (Baker et al., 1990), possibly because p53 levels in normal cells are kept at low level by rapid turnover (Rogel et al., 1985). In addition, the intrinsic genomic instability of tumor cells, which would normally induce the apoptotic pathway, may also be a significant factor in contributing to the induction p53-mediated apoptosis in response to artificially induced DNA damage, such as chemotherapy or radiation therapy. Thus the apparent specificity of p53 for tumor cells would allow the selective targeting of p53-specific suppression, which would be less toxic than tumor cell suppression protocols that aim at a general cell cycle block. While conventional therapies such as chemotherapy and radiotherapy are by themselves non-specifically toxic to normal dividing cells, targeting of tumors that have unstable genomes with inhibitors of DNA repair mechanisms may prevent tumor cells from repairing DNA damage caused by DNA damaging agents, and thus proceed to the p53-mediated apoptotic pathway.

It also is contemplated that other tumor suppressors, for example p21 and MSH-2, will function in an analogous manner to p53 for the purpose of inducing apoptosis. Thus, reference to the use of p53 implicitly includes reference to these and other tumor suppressors to the extent that they are involved with apoptotic mechanisms.

B. DNA Repair Mechanisms and Inhibition of DNA Repair

Treatment of tumor cells with DNA damaging agents results in the induction of DNA repair mechanisms. The success or failure of DNA repair may have a significant role in determining the consequences of p53 expression in a cell subjected to DNA damage. Tumor cells that fail to repair DNA damage, arising from either intrinsic genomic instability or from external DNA damaging agents, may be more susceptible to p53-mediated apoptosis. Several studies suggest that up-regulated DNA repair occurs in cells that have become resistant to DNA damaging agents such as cisplatin. This is evidenced by the fact that expression of DNA repair enzymes, including dTMP synthetase, DNA polymerase B, topoisomerase I, and hMTII-A, is up-regulated. Some of these DNA repair enzymes are subject to transcriptional transactivational by the transcription factor, AP-1, which consists of subunits fos and jun.

Figure 4:
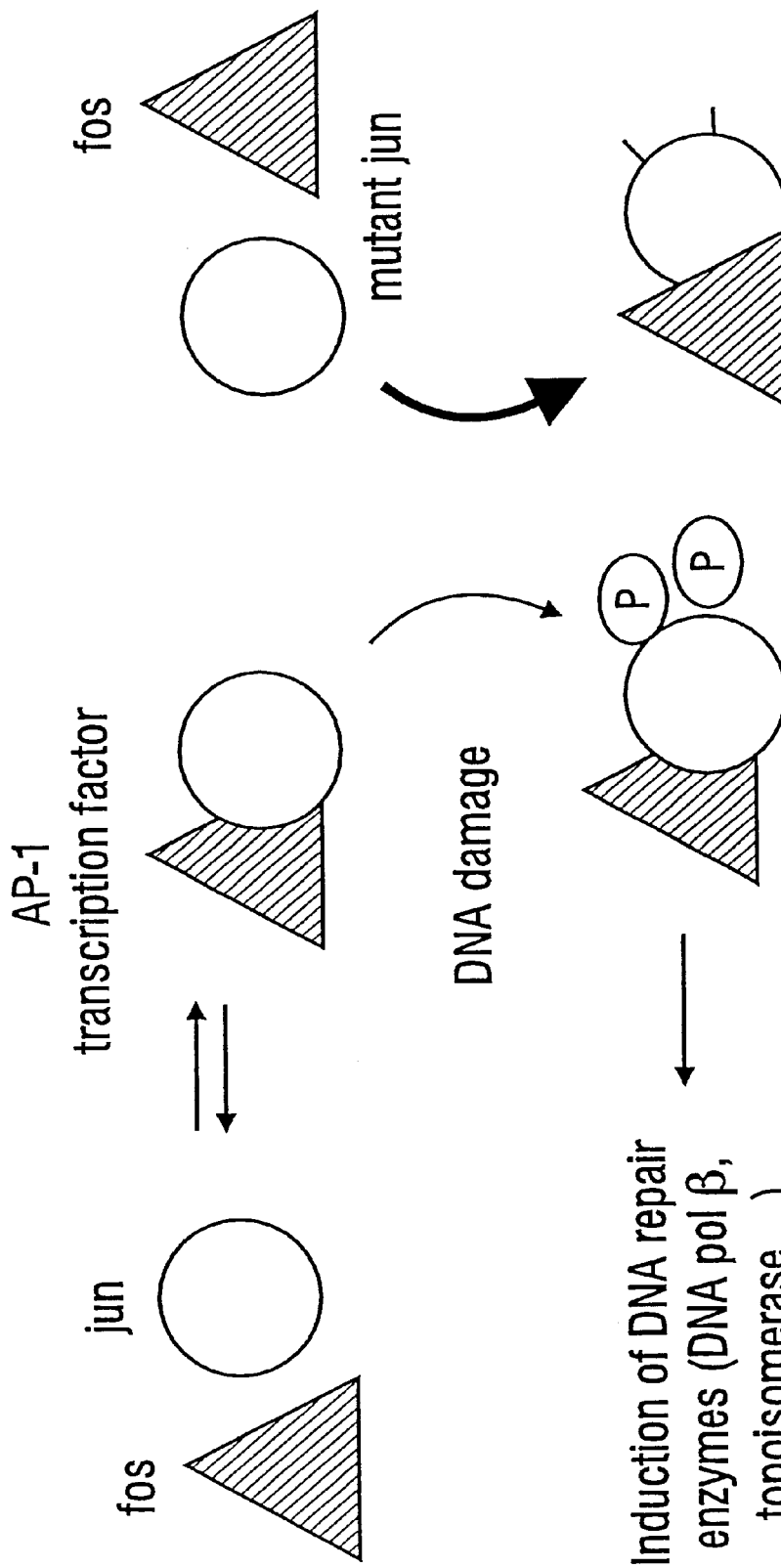
FIG. 4. Model of AP-1 involvement in DNA repair. Wild-type fos and jun form a transcription factor complex AP-1, which upon DNA damage is phosphorylated on jun at position 63 and 73. Phosphorylated AP-1 is involved in the initiation of transcription of DNA repair enzymes. Mutant jun has substitutions of alanine for serine at positions 63 and 73, and thus forms an inactive AP-I complex upon DNA damage, and cannot induce transcription of DNA repair enzymes.

Inhibition of DNA repair mechanisms results in the increased sensitivity of tumor cells to apoptosis induced by DNA damaging agents. For example, DNA repair in tumor cells is down-regulated by a dominant-negative inhibitor of c-jun (mutant jun or m-jun), which fails to be phosphorylated due to amino acid substitutions at two critical phosphorylation sites that are associated with cellular transformation. The m-jun competes with wild-type jun for binding to c-fos so that when m-jun is bound to c-fos, it forms an inactive AP-1 complex, which cannot carry out transactivational of DNA repair genes (FIG. 4.). However, normal cellular activity of AP-1 is not dependent on DNA damage-induced phosphorylation of jun, thus m-jun does not interfere with normal cellular transcription involving AP-1. Cells having the mutant jun gene are more sensitive to p53-induced apoptosis.

Other mechanisms of DNA repair inhibition include inhibitors of other transcription factors, such as Sp1, E2F-1 and jun/ATF2 that may be involved with transcription of DNA damage repair proteins. The included, but are not limited to, uracil DNA glycosylase, alkyl-N-purine DNA glycosylase, DNA ligase IV, DNA ligase III, Hap-1 (Ref-1), poly-ADP-ribose polymerase, dTMP synthetase, DNA polymerase B, topoisomerase I, hMTII-A and DNA-dependent protein kinase. Tissue-specific transcription factors that are involved in DNA repair may also be targeted to provide specific therapy for a particular type of cancer. In one embodiment, nucleic acids encoding antisense inhibitory agents relating to each of these targets, or any of the other transcription factors and DNA repair enzymes, may be used to inhibit the induction of DNA repair.

Organochemical compounds also may be employed to inhibit repair of DNA repair. Such compounds include retinoids like SR11220, and 3-aminobenzamide. Retinoids in general induce a block in the cell cycle. SR11220 is a synthetic retinoid that is specific for AP-1, and thus has less toxicity than other retinoids such as retinoic acid, which has broad specificity (Fanjul et al., 1994; incorporated herein by reference). Other retinoids which may be used to inhibit DNA repair include, but are not limited to, trans-retinoic acid, 9-cis retinoic acid, known to inhibit AP-1, and the synthetic retinoids SR11105, SR11217, SR11238, SR11235, SR11302, SR11220, SR11327, SR11228, SR11324 (Fanjul et al, 1994). The use of retinoids with broad specificity, while, if administered intravenously could be significantly toxic, may exhibit only local toxicity it administered intra-tumorally or at the.

3-aminobenzamide is an inhibitor of poly-ADP ribose polymerase that inhibits the repair of both single- and double-strand breaks induced by DNA damaging agents. It has been shown that p53 is induced following irradiation of 3-aminobenzamide treated cells (Lane, 1992). Compounds with similar specificity could be used according to the present invention. Again, although such compounds may exhibit marked toxicity if used systematically, the regional or local delivery may obviate much of the toxicity. For example, delivery of 3-aminobenzamide as a bolus injection into the tumor mass or the tumor vasculature may result in induction of apoptosis in tumor cells with only minor effects on the surrounding normal tissues.

C. Assays for Other Agents Capable of Inhibiting DNA Repair Activity

In certain embodiments, the present invention concerns a method for identifying compounds that will inhibit DNA repair activity without affecting p53 function. It is contemplated that this screening technique will prove useful in the general identification of compounds that will induce an increase in p53-mediated apoptosis in cancer cells.

Useful compounds may include fragments or parts of the enzymes or factors listed above, including antisense oligonucleotides corresponding to DNA repair-related enzymes. Common antisense targets are regions involve with transcription initiation, translation initiation and splicing. Alternatively, compounds isolated from natural sources, such as animals, bacteria, fungi, plant sources, including leaves and bark, and marine samples may be assayed as potentially useful pharmaceutical agents. It will be understood that the pharmaceutical agents to be screened also could be derived or synthesized from chemical compositions or man-made compounds.

A method for determining the ability of a candidate substance to inhibit the DNA repair activity of cancer cells and to concomitantly induce apoptosis in said cells, the method including generally the steps of:

(a) providing a cell with wild-type p53 function;
(b) admixing a candidate substance and a DNA-damaging agent with the cell;
(c) determining the condition of the cell; and
(d) comparing the condition of the cell with a genetically similar cell treated with the DNA-damaging agent in the absence of the candidate substance.

In a preferred embodiment, the cell is a cancer cell that has heightened DNA repair mechanisms. Because of these mechanisms, the cancer cell is resistant, to a certain extent, to p53-induced apoptosis. In an alternative embodiment, the cell may be p53-negative, but a p53 transgene may be provided in step (b) to facilitate induction of apoptosis.

In one embodiment, the candidate screening assay relies on the formation of lesions in DNA, such as those caused by DNA damaging agents. These lesions block the progression of the Taq polymerase used in PCR™ and thus decrease the yield of the PCR™ product. It has been shown that the level of DNA damage induced by cisplatin, for example, correlates closely with the level of amplified PCR™ product obtained. Measurement of the PCR™ signal obtained from amplification of a significantly large region of DNA, for example 2.7 kB, will decrease in relation to the signal from a small region of amplified DNA, for example 150 bp, whose signal will not be affected due to its small size, after treatment with DNA damaging agents.

Alternatively, it may be desirable simply to measure inhibition of growth of cancer cells, for example, by measuring growth according to the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Assays may be conducted as described by Mosmann et al., (1983) and Rubinstein et al. (1990) (incorporated herein by reference). Therefore, if a candidate substance exhibited inhibition of growth of cancer cells in this type of study, it would likely be a suitable compound for use in the present invention.

Another method of measuring the effects of candidate compounds will be the determination of apoptosis by TUNEL assay. Terminal deoxynucleotidyl transferase mediated dUTP-biotin nick end labeling (TUNEL) assay measures the integrity of DNA and is performed as described by Fujiwara et al., 1994. Briefly, the cells are fixed and cytospun on the slide. Cells are incubated in TdT buffer (30 mM Tris Hcl, pH 7.2; 140 mM cacodylate, 1 mM cobalt chloride) and incubated with biotinylated dUTP (Boehringer Mannheim, Indianapolis, Ind.) and 100 U/ml TdT enzyme (Bethesda Research Laboratory) for 1 h at 37° C. The avidin-biotin complex was detected using the Vectastain Elite kit (Vector Laboratory, Burlingame, Calif.), by the diaminobenzidine-$H_2O_2$ method.

Quantitative in vitro testing of the DNA repair inhibiting agents is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context.

D. p53 Mutations in Cancer p53 currently is recognized as a tumor suppressor gene (Montenarh, 1992). The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 393-amino-acid phosphoprotein that can form complexes with host proteins such as large-T antigen and E1B. The wild-type protein is found in normal tissues and cells, but at concentrations which are minute by comparison with levels of mutant protein in transformed cells or tumor tissue. Interestingly, wild-type p53 appears to be important in regulating cell growth and division. Overexpression of wild-type p53 has been shown in some cases to be anti-proliferative in human tumor cell lines. Thus p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Mis-sense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, some of these negative alleles appear to be tolerated in the organism and passed on in the germ line. Various mutant alleles appear to range from minimally dysfunctional to strongly penetrant (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects.

E. Treatment of p53-Positive Cancers Using Agents that Inhibit DNA Repair.

According to the present invention, a patient with cancer will be treated with various agents that permit p53 induced apoptosis to occur. These agents include DNA repair inhibitory agents and, in certain cases, DNA damaging agents. Because p53 function is necessary, it is desirable that the p53 status of the tumor cells be determined. This may be accomplished using conventional methods, examples of which are described below. Optimally, patients will have adequate bone marrow function (defined as peripheral absolute granulocyte count of>2,000/mm$^3$ and platelet count of 100,000/mm$^3$), adequate liver function (bilirubin≦1.5 mg/dl) and adequate renal function (creatinine<1.5 mg/dl).

The patient will be treated with a pharmaceutically acceptable form of the DNA repair inhibitory agent. These agents are described above. This administration could be in the form of, for example, an intratumoral injection, or indeed any other method of application that is routinely used and well know to one of skill in the art. A more detailed discussion of formulations and routes of administration is provided below.

1. Determination of p53 status of Cells.

A wide variety of detection methods can be employed in the present invention to detect the p53 status of a cell. There are numerous antibodies to the p53 protein, hence any assay that utilizes antibodies for detection, for example, ELISAs, Western Blotting, immunoassay techniques, etc. Alternatively, assays that employ nucleotide probes may be used to identify the presence/absence of p53, for example, Southern blotting, Northern blotting or PCR™ techniques. All the above techniques are well known to one of skill in the art and could be utilized in the present invention without undue experimentation.

i. ELISAs, Immunoassay and Immunohistological assay.

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the anti-p53 antibodies are immobilized on a selected surface, such as a well in a polystyrene microtiter plate, dipstick or column support. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is known as a "sandwich ELISA". Detection also may be achieved by the addition of a second antibody specific for the desired antigen, followed by the addition of a third antibody that has binding affinity for the second antibody, with the third antibody being linked to a detectable label.

Variations on ELISA techniques are know to those of skill in the art. In one such variation, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chcmiluminescent one. The use of such labels is described in U.S. Pat. Nos. 5,310,687, 5,238,808 and 5,221,605.

Assays for the p53 status of the cell may be performed directly on biopsy samples. Methods for in vitro situ analysis are well known and involve assessing binding of antigen-specific antibodies to tissues, cells or cell extracts. These are conventional techniques well within the grasp of those skilled in the art. For example, the antibodies to p53 may be used in conjunction with both fresh-frozen and formalin-fixed, paraffin-embedded tissue blocks prepared for study by immunohistochemistry (IHC). Each tissue block may consist of 50 mg of residual "pulverized" tumor. The method of preparing tissue blocks from these particulate specimens has been successfully used in previous IHC studies of various prognostic factors, e.g., in breast cancer, and is well known to those of skill in the art. (Abbondanzo et al., 1990; Allred et al., 1990; Brown et al., 1990)

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

ii. Southern and Northern Blotting Techniques

Southern and Northern blotting are commonly used techniques in molecular biology and well within the grasp of one skilled in the art.

The DNA and RNA from test cells is recovered by gentle cell rupture in the presence of a cation chelator such as EDTA. The proteins and other cell milieu are removed by admixing with saturated phenol or phenol/chloroform and centrifugation of the emulsion. The DNA and RNA is in the upper aqueous phase, it is deproteinised and mixed with ethanol. This solution allows the DNA and RNA to precipitate, the DNA and RNA can then be recover using centrifugation. In the case of RNA extraction, RNAse inhibitors such as DEPC arc needed to prevent RNA degradation.

Electrophoresis in agarose or polyacrylamide gels is the most usual way to separate DNA and RNA molecules. Southern blotting will confirm the identity of the p53 encoding DNA. This is achieved by transferring the DNA from the intact gel onto nitrocellulose paper. The nitrocellulose paper is then washed in buffer that has for example, a radiolabelled cDNA containing a sequence complementary to wild-type-P53 DNA. The probe binds specifically to the DNA that encodes a region of p53 and can be detected using autoradiography by contacting the probed nitrocellulose paper with photographic film. p53-encoding mRNA can be detected in a similar manner by a process known as Northern blotting. For a more detailed description of buffers gel preparation, electrophoresis condition etc., the skilled artisan is referred to Sambrook, 1989.

iii. Polymerase Chain Reaction (PCR™)

PCR™ is a powerful tool in modern analytical biology. Short oligonucleotide sequences usually 15–35 bp in length are designed, homologous to flanking regions either side of the p53 sequences to be amplified. The primers are added in excess to the source DNA, in the presence of buffer, enzyme, and free nucleotides. The source DNA is denatured at 95° C. and then cooled to 50–60° C. to allow the primers to anneal. The temperature is adjusted to the optimal temperature for the polymerase for an extension phase. This cycle is repeated 25–40 times.

In particular the present invention uses PCR™ to detect the p53 status of cells. Mutations in the p53 gene are first detected with Single Strand Conformation Polymorphism (SSCP) which is based on the electrophoretic determination of conformational changes in single stranded DNA molecules induced by point mutations or other forms of slight nucleotide changes. To identify where the mutation is located at within the p53 gene, each exon is separately amplified by PCR™ using primers specific for the particular exon. After amplification, the PCR™ product is denatured and separated out on a polyacrylamide gel to detect a shift in mobility due to a conformational change which resulted because of a point mutation or other small nucleotide change in the gene. Mutations result in a change in the physical conformation of the DNA as well as change in the electrical charge of the molecule. Thus during electrophoresis when an electrical charge is applied to the molecule, DNA that is slightly different in shape and charge as compared to wild-type will move at a different rate and thus occupy a different position in the gel.

After determination of which DNA fragment contains the mutation, the specific nucleotide changes are detected by DNA sequencing of the amplified PCR™ product. Sequencing of linear DNA breaks down the DNA molecule into its individual nucleotides in the order with which they are assembled in the intact molecule. Separation of the individual nucleotides by electrophoresis on a sequencing gel allows detection of individual nucleotide changes compared to wild-type and is used to determine homo- or heterozygocity of a mutation, which is easily distinguished by the appearance of a single or double band in the sequencing gel.

2. Pharmaceutical Compositions and Routes of Administration

Aqueous compositions of the present invention will have an effective amount of a p53 expression vector or p53 protein, along with a compound that inhibits DNA repair. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains a compound or compounds that increase the expression of wild-type p53 will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention also may be prepared in forms suitable for topical administration, such as in cremes and lotions. These forms may be used for treating skin-associated diseases, such as various sarcomas.

Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery to the lung is contemplated. Volume of the aerosol is between about 0.01 ml and 0.5 ml. Similarly, a preferred method for treatment of colon-associated disease would be via enema. Volume of the enema is between about 1 ml and 100 ml. Direct intratumoral injection is the preferred mode, with continuous intratumoral perfusion a more specific embodiment.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance. For the instant application, it is envisioned that the amount of therapeutic composition comprising a unit dose will range from about 5–30 mg of polynucleotide.

3. Kits

All the essential materials and reagents required for determining wild-type p53 in a sample or for inhibiting the DNA repair mechanisms in tumor cells may be assembled together in a kit. When the components of the kit are provided in one or more liquid solutions, the liquid solution preferably is an aqueous solution, with a sterile aqueous solution being particularly preferred.

For the detection of wild-type p53, the kit may contain materials for PCR™ analyses, such primers, buffers and appropriate solvents. Alternatively, if the detection is via immunologic means, the kit may contain antibodies directed to the p53, secondary antibodies that binding primary antibodies, labels or signal generating compounds (either conjugated or unconjugated) and various reagents for the generation and detection of signals.

For in vivo use, an inhibitor of DNA repair, in combination with an p53 expression vector may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the inhibitor of DNA repair and/or the p53 status determining agents, for explaining the assays for determining p53 levels in samples.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

F. Treatment of p53-Negative Cancers: Combining Agents that Inhibit DNA Repair and Gene Therapy In a separate embodiment of the present invention, it is envisioned that inhibitors of DNA repair will be used in combination with gene therapy in the treatment of those cancers that do not express a functional p53. It is clear that delivery of wild-type p53 into tumors that express a mutated p53 gene can overcome the deleterious effects of the p53 mutation. In the present embodiment of the invention, an inhibitor of DNA repair can be administered concurrently with the gene therapy, before the gene therapy or after the gene therapy. The components need for gene therapy, as well as the therapeutic inhibitors of DNA repair, can be assembled in a kit form as described above. The inhibitors of DNA repair also have been described above, so the remaining discussion relates to the elements relating to gene delivery.

1. Expression Vectors

Throughout this application, the term "expression construct" is meant to include any type of genetic construct containing a nucleic acid coding for a p53 product. In order for the construct to effect expression, the polynucleotide encoding the p53 polynucleotide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used herein to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a p53 polynucleotide is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the p53 polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of p53 polynucleotides. Table 1 lists several promoters which may be employed, in the context of the present invention, to regulate the expression of p53 constructs. This list is not intended to be exhaustive of all the possible elements involved in the promotion of p53 expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance: this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a p53 construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 1

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $α_1$-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

Further, selection of a promoter that is regulated in response to specific physiologic signals can permit inducible expression of the p53 construct. For example, with the polynucleotide under the control of the human PAI-1 promoter, expression is inducible by tumor necrosis factor. Table 2 illustrates several promoter/inducer combinations:

TABLE 2

| Element | Inducer |
| --- | --- |
| MT II | Phorbol Ester (TPA) Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester (TPA) |

TABLE 2-continued

| Element | Inducer |
| --- | --- |
| Tumor Necrosis Factor | FMA |
| Thyroid Stimulating Hormone α Gene | Thyroid Hormone |

In certain embodiments of the invention, the delivery of an expression vector in a cell may be identified in vitro or in vivo by including a marker in the expression vector. The marker would result in an identifiable change to the transfected cell permitting identification of expression. Usually, the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding p53. Further examples of selectable markers are well known to one of skill in the art.

One will typically include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

In preferred embodiments of the present invention, the expression construct comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes (discussed below), expression vectors need not be viral but, instead, may be any plasmid, cosmid or phage construct that is capable of supporting expression of encoded genes in mammalian cells, such as pUC or Bluescript™ plasmid series.

i. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a p53 is inserted into the viral genome in the place of certain viral sequences to produce a virus that is replication-defective. In order to produce virions, a packaging cell line containing the gag, pol and env genes but without the LTR and ψ components is constructed (Mann et al., 1983). When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

ii. Adenoviruses

Human adenoviruses are double-stranded DNA tumor viruses with genome sizes of approximate 36 kb (Tooze, 1981). As a model system for eukaryotic gene expression, adenoviruses have been widely studied and well characterized, which makes them an attractive system for development of adenovirus as a gene transfer system. This group of viruses is relatively simple to grow and manipulate, and exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, el al., 1977) have been developed to provide the essential viral proteins in trans. The inventor thus reasoned that the characteristics of adenoviruses rendered them good candidates for use in targeting cancer cells in vivo (Grunhaus and Horwitz, 1992).

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus and Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991). Surprisingly persistent expression of transgenes following adenoviral infection has also been reported.

Adenovirus-mediated gene transfer has recently been investigated as a means of mediating gene transfer into eukaryotic cells and into whole animals. For example, in treating mice with the rare recessive genetic disorder ornithine transcarbamylase (OTC) deficiency, it was found that adenoviral constructs could be employed to supply the normal OTC enzyme. Unfortunately, the expression of normal levels of OTC was only achieved in 4 out of 17 instances (Stratford-Perricaudet et al., 1990). Therefore, the defect was only partially corrected in most of the mice and led to no physiological or phenotypic change. These type of results therefore offer little encouragement for the use of adenoviral vectors in cancer therapy.

Attempts to use adenovirus to transfer the gene for cystic fibrosis transmembrane conductance regulator (CFTR) into the pulmonary epithelium of cotton rats have also been partially successful, although it has not been possible to assess the biological activity of the transferred gene in the epithelium of the animals (Rosenfeld et al., 1992). Again, these studies demonstrated gene transfer and expression of the CFTR protein in lung airway cells but showed no physiologic effect. In the 1991 Science article, Rosenfeld et al. showed lung expression of a1-antitrypsin protein but again showed no physiologic effect. In fact, they estimated that the levels of expression that they observed were only about 2% of the level required for protection of the lung in humans, i.e., far below that necessary for a physiologic effect.

The gene for human a1-antitrypsin has been introduced into the liver of normal rats by intraportal injection, where it was expressed and resulted in the secretion of the introduced human protein into the plasma of these rats (Jaffe et al., 1992). However, and disappointingly, the levels that were obtained were not high enough to be of therapeutic value.

These type of results do not demonstrate that adenovirus is able to direct the expression of sufficient protein in recombinant cells to achieve a physiologically relevant effect, and they do not, therefore, suggest a usefulness of the adenovirus system for use in connection with cancer therapy. Furthermore, prior to the present invention, it was thought that p53 could not be incorporated into a packaging cell, such as those used to prepare adenovirus, as it would be toxic. As E1B of adenovirus binds to p53, this was thought to be a further reason why adenovirus and p53 technology could not be combined.

iii. Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. These viruses offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. in vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

2. Alternative Methods for Gene Delivery

In order to effect expression of p53 constructs, the expression vector must be delivered into a cell. As described above, the preferred mechanism for delivery is via viral infection where the expression vector is encapsidated in an infectious adenovirus particle.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use.

In one embodiment of the invention, the adenoviral expression vector may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an p53 construct may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding a p53 construct may be delivered via this method.

In a further embodiment of the invention, the expression vector may be entrapped in a liposome. Liposomes are vesicular structures characterized by a phospholipid bilayer membrane and an inner aqueous medium. Multilamellar liposomes have multiple lipid layers separated by aqueous medium. Liposomes form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacteriophage promoter is employed in the DNA construct, it also will be desirable to include within the liposome an appropriate bacteriophage polymerase.

Another mechanism for transferring expression vectors into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an adenoviral expression vector also may be specifically delivered into a cell type such as lung, epithelial or tumor cells, by any number of receptor-ligand systems, with or without liposomes. For example, epidermal growth factor (EGF) may be used as the receptor for mediated delivery of p53 construct in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods. During ex vivo culture, the expression vector can express the p53 construct. Finally, the cells may be reintroduced into the original animal, or administered into a distinct animal, in a pharmaceutically acceptable form by any of the means described below.

G. Combination Therapy

Tumor cell resistance to DNA damaging agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent gancyclovir (Culver, et al., 1992). In the context of the present invention, it is contemplated that inhibitors of DNA repair mechanisms and p53 gene therapy could be used similarly in conjunction with chemo- or radiotherapeutic intervention.

To induce apoptosis in cells, such as malignant or metastatic cells, using the methods and compositions of the present invention, one would generally contact a "target" cell with an inhibitor of DNA repair (and additionally with a wild-type p53 protein or expression vector containing wild-type p53 if the cell is p53-negative), and at least one DNA damaging agent. These compositions would be provided in a combined amount effective to induce apoptosis; this may include elimination or diminution of the related tumor burden, or it may simply inhibit proliferation of the related tumor.

This process may involve contacting the cells with an inhibitor of DNA repair (and optionally wild-type p53 expression vector) and the DNA damaging agent(s) at the same time. This may be achieved by contacting the cell with a single composition or pharmacological formulation that includes both agents, or by contacting the cell with two distinct compositions or formulations, at the same time, wherein one composition includes the inhibitor of DNA repair and a wild-type p53 protein or expression vector containing wild-type p53, and the other includes the DNA damaging agent.

Alternatively, the inhibitor of DNA repair and p53 gene therapy treatment may precede or follow the DNA damaging agent treatment by intervals ranging from minutes to weeks. In embodiments where the DNA damaging factor, and the inhibitor of DNA repair and p53 gene therapy are applied separately to the cell, one would generally ensure that a significant period of time did not expire between the time of each delivery, such that the DNA damaging agent, and inhibitor of DNA repair and p53 gene therapy would still be able to exert an advantageously combined effect on the cell. In such instances, it is contemplated that one would contact the cell with both agents within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the inhibitor of DNA repair and p53 protein or expression vector containing p53, or the DNA damaging agent will be desired. Various combinations may be employed, where "A" is the inhibitor of DNA repair (and optionally a wild-type p53-encoding expression vector) and the DNA damaging agent is "B":

| B/A/A   | A/B/B   | A/B/A   | A/A/B   | B/B/A   | B/A/B   |
|---------|---------|---------|---------|---------|---------|
| or:     |         |         |         |         |         |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |
| A/B/B/B | B/A/B/B |         |         |         |         |

The terms "contacted" and "exposed", when applied to a cell, are used herein to describe the process by which a protein or compound, such as an inhibitor of DNA repair, expression vector and a DNA damaging agent or factor are delivered to a target cell by placement in direct juxtaposition with the target cell. To induce apoptosis, both agents are delivered to a cell in a combined amount effective to induce apoptosis of the cell.

DNA damaging agents or factors are defined herein as any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP), carboplatin, bisulphan, melphalan, chlorambucil, ifosfamide, merchlorehtamine, nitrosourea, tenoposide, daunorubicin, doxorubicin, dactinomycin, plicamycin, anthracyclines, taxol, taxotere and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with an inhibitor of DNA repair and a p53 protein or gene is particularly preferred as this compound.

Any method may be used to contact a cell with an inhibitor of DNA repair, so long as the method results in inhibition of DNA repair within the cell. This includes both the direct delivery of an inhibitor of DNA repair protein to the cell and the delivery of a gene or DNA segment that encodes the inhibitor of DNA repair, which gene will direct the expression and production of the inhibitor of DNA repair within the cell. In that protein delivery is subject to such drawbacks as protein degradation and low cellular uptake, it is contemplated that the use of a recombinant vector that expresses a inhibitor of DNA repair protein will provide particular advantages.

In treating cancer according to the invention, one would contact the tumor cells with a DNA damaging agent in addition to the inhibitor of DNA repair. This may be achieved by irradiating the localized tumor site with DNA damaging radiation such as X-rays, UV-light, γ-rays or even microwaves. Alternatively, the tumor cells may be contacted with the DNA damaging agent by administering to the subject a therapeutically effective amount of a pharmaceutical composition comprising a DNA damaging compound. The DNA damaging agent may be prepared and used as a combined therapeutic composition, or kit, by combining it with an inhibitor of DNA repair and p53 expression vector, as described above.

Agents that directly cross-link nucleic acids, specifically DNA, are envisaged and are shown herein, to eventuate DNA damage leading to a synergistic anti-neoplastic combination. Agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis, and chromosomal segregation. Such chemotherapeutic compounds include adriamycin, also known as doxorubicin, etoposide, verapamil, podophyllotoxin, and the like. Widely used in clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors, and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to Remington's Pharmaceutical Sciences, 15th Ed., 1990. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the local or regional delivery of an inhibitor of DNA repair, a DNA damaging agent and/or a gene therapy vector expressing p53 to target cancer cells will be an efficient method for therapeutic intervention. Alternatively, systemic delivery of an inhibitor of DNA repair, or the DNA damaging agent may be appropriate in certain circumstances, for example, where extensive metastasis of a has occurred.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

H. Examples

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should , in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE I

Materials and Methods

Cell Lines and Tissue Culture

T98G glioblastoma cells were obtained from ATCC and cultured at 37° C. 10% $CO_2$ in Dulbecco's Modified Eagles Medium supplemented with 10% newborn calf serum. 9L rat glioblastoma cells were obtained from Carol Cruse (University of Colorado) and cultured at 37° C. in 10% $CO_2$ in Dulbecco's Modified Eagles Medium supplemented with 10% fetal Calf serum. The T98G-LHCmjun clone (termed T98G mutant jun or T98G-mjun), as well as control empty vector modified clone (termed T98GLHCX) were obtained from Dr. Dan Mercola (Sidney Kimmel Cancer Center) and were cultured in the same way as were T98G cells except that 100 μg/ml hygromycin was added to the culture medium. The 98G-mjun is stably modified to express a dominant negative mutant of c-jun (the mutant was obtained by site-directed mutagenesis by M. Karin and colleagues and is described by Smeal et al. (1991). Mutant jun has ser→ala substitutions at positions 63 and 73, two sites of DNA damage-induced phosphorylation, and can therefore not be phosphorylated at these sites. 9LpCEPp53 (or 9LpCEP4, control) were cultured in the same way at 9L cells except that 50 μg/ml hygromycin was added to the medium.

Chemicals

Cisplatin (Platinol™, Bristol Myers/Squibb) was obtained as a 1 mg/ml aqueous solution through local pharmacies. This solution was diluted to 0.3 mg/ml (1 mM aliquoted, and stored in the dark at 20° C. 3-Aminobenzamide was purchased from Sigma Chemical Company, St. Louis, Mo.). The synthetic retinoid SR11220 was supplied by Dr. Magnus Pfahl, Sidney Kimmel Cancer Center. This retinoid has been demonstrated to have anti-AP-1 activity (Fanjul et al., 1994).

Plasmids pCEP4 was purchased from Invitrogen (San Diego, Calif.) When transduced into mammalian cells, this plasmid replicates as an independent cytoplasmic episome as a result of its EBV origin of replication. pCEP4 encodes the EBNA-1 protein needed for replication, and a hygromycin resistance marker. Transgene expression is driven by the CMV promoter. The reporter plasmid PG13 ($PG_{13}$-CAT) was obtained from Bert Vogelstein (Johns Hopkins Oncology Center). In this plasmid, the chloramphenicol acetyl transferase (CAT) gene is under the control of a wild -type p53-specific binding site. Cells to be assayed for wild-type p53 expression are transduced (using Lipofectamine (GIBCO/BRL, Gaithersberg, Md.) and following the manufacture's instructions) wit PG 13 and incubated for two days. Two days following transfection, cell lysates are prepared and analyzed for their ability to acetylate $^{14}C$-chloramphenicol by thin-layer chromatography. (See Ausubel et al., 1992 and Kern et al., 1992). Chromatographs were analyzed by autoradiography or quantitated with and Ambis4000 Radioanalytic Imaging system (Ambis, Inc., San Diego, Calif.).

Selection of Rat 9L Cells Expressing Human Wild-Type p53

Rat 9L glioblastoma cells express p53 mutated at codon 277 (J. Neuroonal. 19:259–268, 1994.) 9LpCEPp53 (or 9LpCEP$_4$) were obtained by transducing 5×10$^5$ 9L cells with 15 μG of pCEPp53 (or pCEP4) using Lipofectamine (GIBCO/BRL, Gaithersberg, Md.) following the manufacturer's instructions. Clones were selected in 50 μg/ml hygromycin and characterized for wild-type p53 expression by immunoprecipitation (immunoprecipitation procedure described in: Gjerset et al., Molec. Carcinog. 5:190–198, 1992) using the 1801 anti-p53 antibody specific for human p53 (p-Ab-2, Oncogene Science, Uniondale, N.Y.), and by the PG13 functional assay described above. pCEPp53 was derived by inserting the human wild-type p53 cDNA into the multicloning site of pCEP4.

Viruses and Infections p53 adenovirus or β-galactosidase (β-gal) adenovirus were obtained from Canji, Inc. (San Diego, Calif.). These are replication-defective viruses in which the early region genes E1A and E1B, which are required for viral replication, are deleted and replaced with the human wild-type p53 and β-gal sequences, respectively, each form viral CMV promoter (Wills et al., 1994).

Cells were infected when they were at 80% confluence with either 100 pfu per cell overnight in DMEM containing 2% heat-inactivated FBS (for T98G and clones derived from T98G) or at 50 pfu per cell for 2 hours (9L cells). The efficiency of infection was determined by staining a sample of the β-gal virus-infected cells at 48 hrs post-infection as described (Dannenerg and Saga, 1981). Under the infection conditions used, β-gal expression was observed in 95–100% of the cell population.

Cell Viability Assays

Viability assays were performed in 96 wells plates 6–7 days after plating. Cells were plated at a starting cell number per well of 1000. Triplicate or quadruplicate wells were set up for each assay point. For cisplatin treatment, triplicate or quadruplicate wells were set up for each assay point. For cisplatin treatment, triplicate or quadruplicate wells were exposed for 1 hour to various concentrations of cisplatin (Platinol™), and then incubated in the absence of cisplatin for 7 days, during which time control (untreated) wells were in exponential phase growth. Viable cell number was based on the bioconversion of the tetrazolium compound, MTS, into formazan (Promega, Celltiter96™Aq$_{eous}$), as determined by absorbance at 590 nm using an ELISA reader. For 3-aminobenzamide (ABZ) treatment, triplicate or quadruplicate wells were treated with either 5 mM ABZ or 10 mM ABX. Fresh ABZ was added every two days and viability was scored as described above at 6 days. Assays involving the synthetic retinoid SR11220 were performed in the presence of charcoal-treated fetal bovine serum. Medium was replaced every two days with medium containing fresh retinoid.

PCR™ Stop Assay for DNA Damage

This assay has been described (Oshita and Saijo, 1994; Jannerwein and Eastman, 1991). The assay is based on the principle that every DNA lesion, including adducts produced by cisplatin, can potentially block the progression of the Taq polymerase and decrease the yield of a given PCR™ product. It has been well demonstrated that the degree of inhibition of PCR™ correlates with the level of platination, indicating that the polymerase is inhibited by every lesions (Jannerwein and Eastman, 1991). Furthermore, when whole cells are incubated with varying levels of cisplatin, the degree of inhibition of amplification of a specific PCR™ product from DNA purified from these cells, correlates closely with the amount of DNA damage (level of DNA platination) as measured by atomic adsorption (Jannerwein and Eastman, 1991). The following primers (used by Oshita and Saijo, 1994) which amplify a 2.7 Kb fragment of the human hypoxanthine phosphoribosyl transferase (HPRTase) gene were used:

5' primer. 5'-TGGGATTACACGTGTGAACCAACC-3' (SEQ ID NO:1)

3' primer. 5'-GATCCACAGTCTGCCTGAGTCACT-3' (SEQ ID NO:2)

As an internal control for the efficiency of the PCR™ reaction, a nested 5' primer which amplifies a 150 bp fragment of the same gene was used:

nested 5' primer: 5'-CCTAGAAAGCACATGGAGAGCTAG-3' (SEQ ID NO:3)

At the cisplatin levels used to treat the cells, damage to the smaller fragment is undetectable. DNA from cells was prepared immediately after a 1 hour 15 minute treatment with cisplatin (100 μM or 200 μM) and 6 hours later. In some experiments, 3-aminobenzamide (10 mM), an inhibitor of ADP ribosylation and DNA repair (see Din et al., 1992) was added during the 6 hour recovery period. Lysates from $5 \times 10^6$ cells were prepared by proteinase K digestion of cells, followed by digestion with BamH1 (which reduces viscosity but does not cut within the HPRTase gene) and Rnase, followed by phenol-chloroform-isoamyl alcohol extraction, and alcohol precipitation. DNA was washed with 70% EtOH to remove salt, followed by 100% EtOH dried briefly, and resuspended at 1 mg/ml in sterile $H_2O$. Quantitative PCR™ was performed in 50 μl aliquots using 0.5 μg DNA, 50 pmol of forward primer for 2.7 Kb fragment, 50 pmol reverse primer, and 5 pmol of forward primer for the 150 base fragment, 50 mM KCL, 10 mM Tris pH 8.3, 1.5 mM $MgCl_2$, 250 mM dNTPs, 0.5 μl Tac polymerasse (Perkin Elmer), and 1 pmol radioactively end-labeled reverse primer (labeled with y-$^{32}$P-dATP). Amplification conditions were as follows: 1 cycle: 94° C., 1'30; 25 cycles: 94° (1 min)-57° (1min)-70°(2'30"); 1 cycle:94°(1 min)-57°(1 min)-70°(7'). Control known amounts of DNA in two-fold dilutions were performed to insure that the extent of reaction was directly proportional to the amount of template Following amplification, 10 μl aliquots were electrophoresed on a 1% agarose gel. The gel was vacuum-dried for two hours onto filter paper and the PCR™-amplified 2.7 Kb and 150 bp bands were quantitated using an Ambis4000 Radioanalytic Imaging system (Ambis, Inc., San Diego, Calif.).

EXAMPLE II

The Effects of DNA Repair Inhibition on the Growth of Cancer Cells

The effects of DNA repair inhibition on the growth of two different types of cancer cells with varying status in wild-type p53 expression were tested.

In the first instance, the following three cell lines were tested: T98G, parental cell line; T98GLHXC, empty vector modified control; T98G-mutant jun, containing jun mutated at positions 63 and 73 from serine to alanine. The cells were infected with wild-type p53-expressing virus and the growth of the cells was measured after seven days (FIG. 1). The T98G-mutant jun cells had a significantly reduced viability compared to the T98G parental cells and the T98GLHXN empty vector control cells. Viability of the p53 adenovirus infected clones was measured relative to the viability of βgal adenovirus-infected control cells for each subclone.

The transcriptional activation of some DNA repair enzymes are controlled by the transcription factor AP-1, which is a complex of the proteins fos and jun. $^{63}$Ser and $^{73}$Ser are important phosphorylation sites on jun during the induction of DNA repair in response to DNA damage. In the present instance, mutation of these amino acids to alanine results in the decreased viability of T98G glioblastoma cells. The proposed mechanism of action of these mutations is through inactivation of AP-1, which then would not be able to transactivate the transcription of DNA repair enzymes (FIG. 4).

Figure 6:
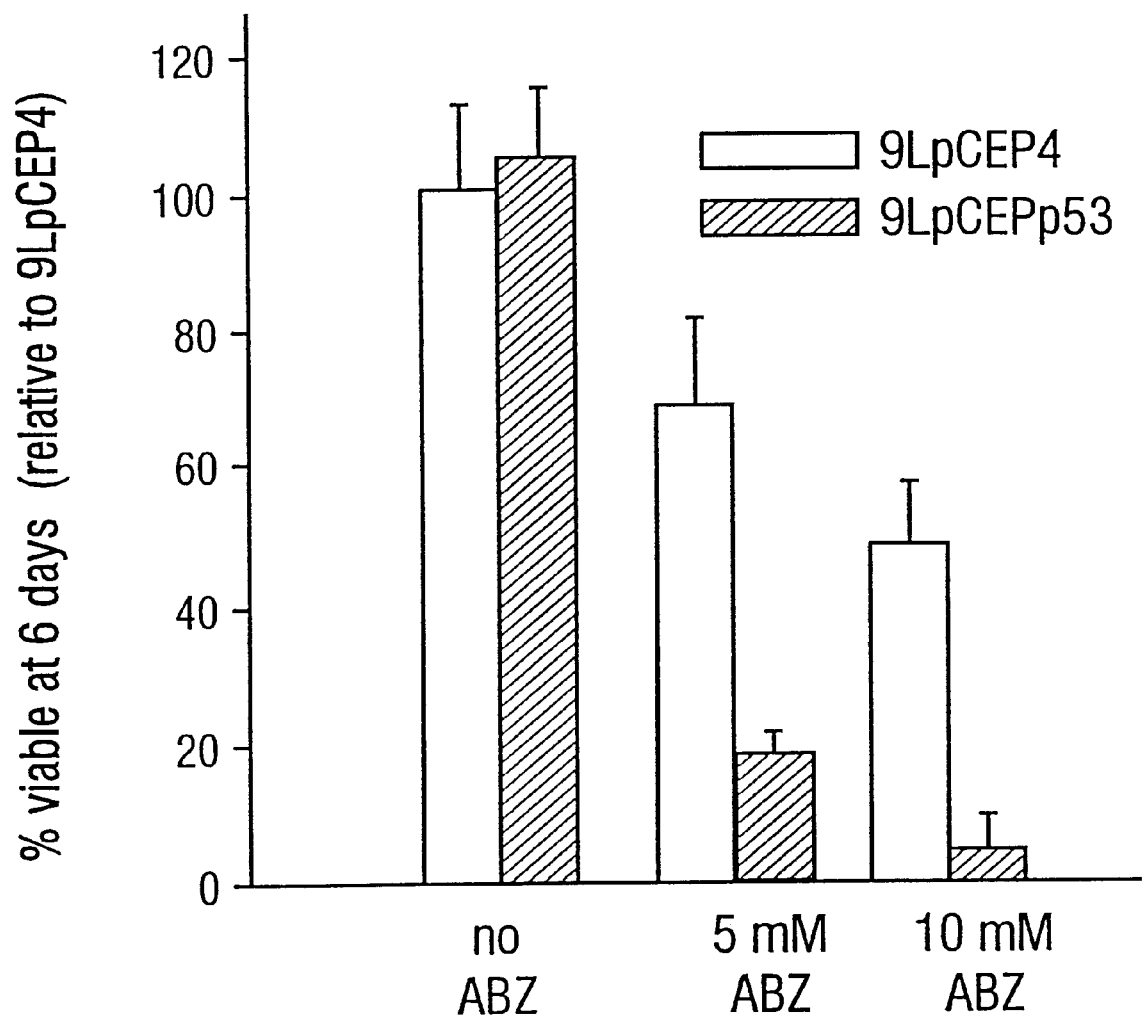
FIG. 6. Cell growth of 9 1 rat glioblastoma cells expressing endogenous mutant p53 were stably modified with vector only (pCEP4, light bars) or human wild-type p53 (pCEPp53 dark bars), and either (sets of bars left to right): untreated; treated for 6 days with 5 mM 3-aminobenzamide (ABZ); or treated for 6 days with 10 mM 3-aminobenzamide (ABZ). Percentage viability was measure at 6 days. Refer to Example I for methods and materials.

In the second instance, 9L rat glioblastoma cells were stably modified with either a control vector, pCEP4, or a vector encoding human wild-type p53, pCEPp53. The cells were then treated with 3-aminobenzamide, an inhibitor of the DNA repair enzyme poly-ADP ribose polymerase (FIG. 6). 9L rat glioblastoma cells that expressed human wild-type p53 exhibited reduced viability in a dose dependent manner, with low viability at 5 mM 3-aminobenzamide and even lower viability at 10 mM 3-aminobenzamide. In contrast, 9L cells stably expressing only the control vector, were resistant to growth inhibition at both 5 mM and 10 mM 3-aminobenzamide. The viability of neither pCEP4 nor pCEPp53 transfected 9L glioblastoma cells was affected in the absence of 3-aminobenzamide treatment. Thus cells that are inhibited for DNA repair are sensitive to p53-mediated growth suppression.

EXAMPLE III

The Combined Effects of DNA Damaging Agents and DNA Repair Inhibitors on Tumor Cells The effects of cisplatin alone and in combination with a synthetic retinoid SR11220 on tumor cells expressing wild-type p53 were tested.

Figure 5:
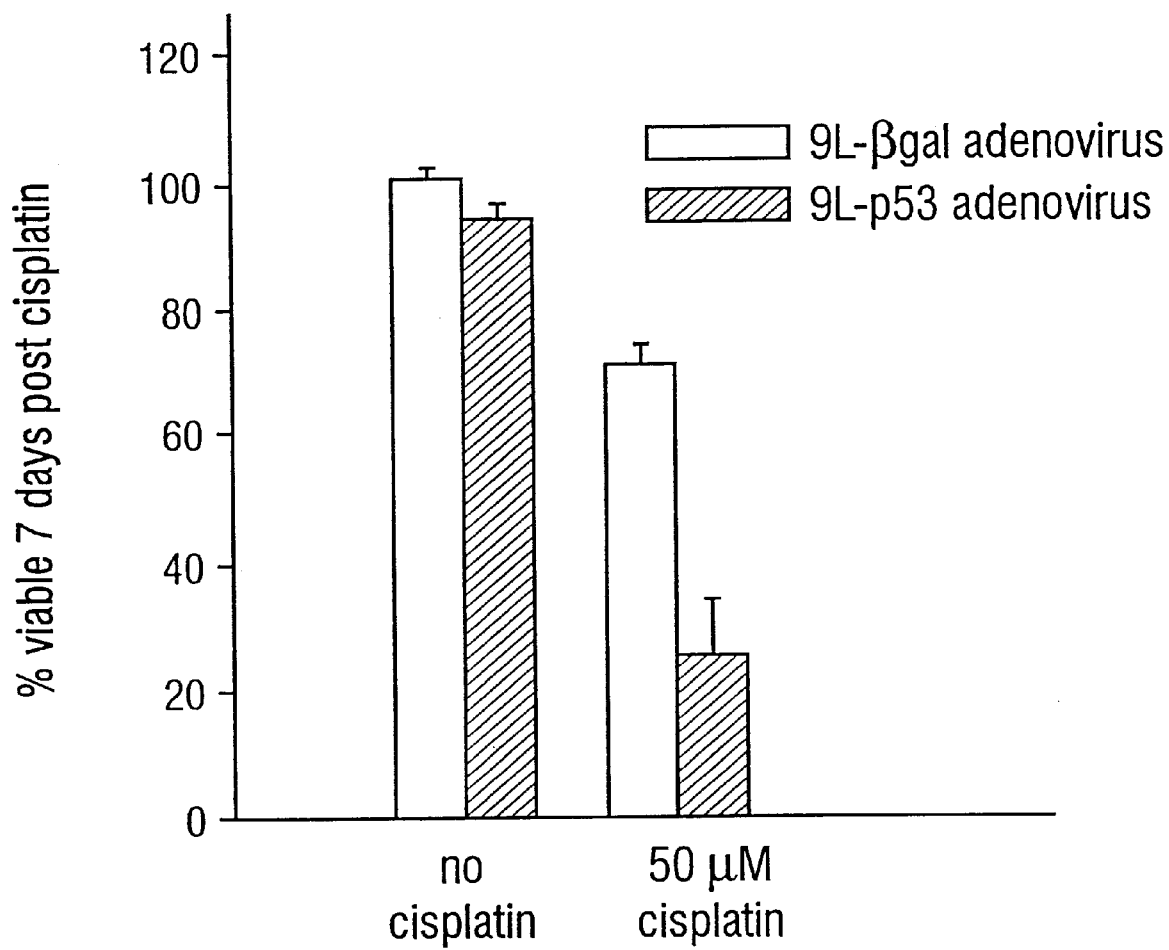
FIG. 5. Cell growth of 9L rat glioblastoma cells expressing an endogenous mutant p53 was measured after infection with a human wild-type p53 adenovirus (light bars) or βgal adenovirus (dark bars) and treated one day later for one hour with (right set of bars) or without (left set of bars) 50 mM cisplatin. Percentage viability was measured 7 days later. Refer to Example I for methods and materials.

In the first instance, viability of 9L rat glioblastoma cells infected with either βgal adenovirus or p53 adenovirus, and treated one day later in the absence or presence of 50 μM cisplatin was measured seven days after administration of cisplatin (FIG. 5). 9L rat glioblastoma cells infected with p53 adenovirus exhibited a significant decrease in viability compared to 9L cells infected with βgal adenovirus when exposed to cisplatin. The viability of 9L rat glioblastoma cells infected with either βgal adenovirus or p53 adenovirus in the absence of cisplatin did not significantly decrease. Thus tumor cells that have sustained DNA damage are more susceptible to growth suppression by p53.

Figure 2:
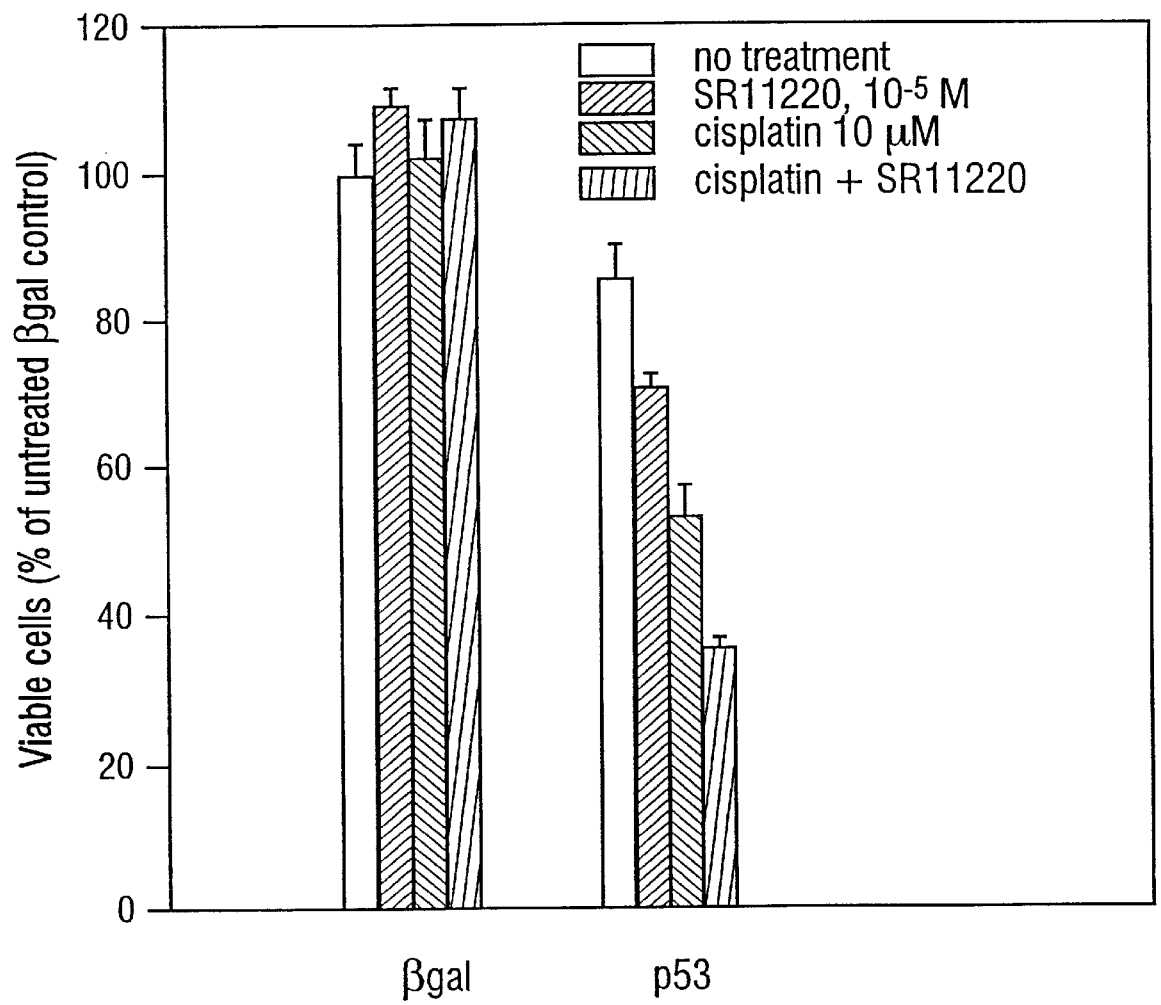
FIG. 2. Cell viability assay. Cell growth was measured after 7 days of βgal adenovirus or p53 adenovirus-infected T47D breast cancer cells under different condition (left to right): no treatment; in the presence of $10^{-8}$ M SR11220; following 1 hour exposure to 10 μM cisplatin; in the presence of $10^{-8}$ M SR11220 and following a 1 hour exposure to cisplatin. Percentage viability is relative to the same conditions in untreated cells infected with βgal-adenovirus.

In the second instance, T47D breast cancer cells were infected with βgal-adenovirus or p53 adenovirus and treated with SR11220 or cisplatin or both. SR11220 is a synthetic retinoid that specifically down-regulates AP-1. Cisplatin is a common chemotherapeutic agent that creates DNA adducts in cells. T47D breast cancer cells infected with p53 adenovirus were slightly sensitive to the effects of p53, in comparison to T47D breast cancer cells infected with βgal-adenovirus (FIG. 2). Upon treatment of p53 adenovirus infected T47D cells with $10^{-8}$ M SR11220, a further reduction in viability was shown. Treatment of p53 adenovirus infected T47D cells with 10 μM cisplatin had an even greater effect on the reduction in viability. Treatment of p53 adenovirus infected T47D cells with a combination if $10^{-8}$ M SR11220 and 10 μM cisplatin further reduced the viability of the tumor cells. In contrast the viability of T47D cells infected with the βgal adenovirus control was not reduced significantly after treatment with SR11220, cisplatin or a combination thereof. Thus the combined effects of a DNA damaging agent and an inhibitor of DNA repair significantly sensitize tumor cells to growth suppression by p53.

EXAMPLE IV

Cisplatin Treatment of Tumor Cells Induces Apoptosis

Figure 3A:
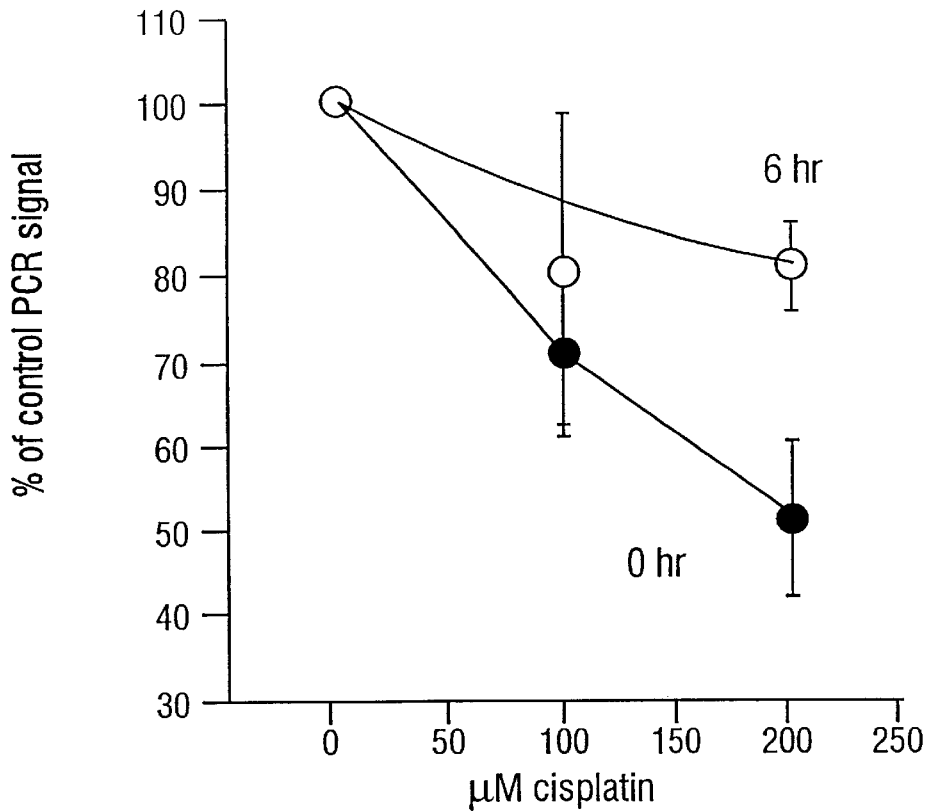
FIG. 3A. DNA damage assay of cisplatin-treated T98G parental cells. DNA damage after zero (closed circles) and six (open circle) hours after a 1.5 hour cisplatin treatment was measured by PCR™ of a 2.7 Kbp region of the HPRT gene and expressed as the percentage of signal observed after PCR™ of a 150 base pair region within the HPRT gene. Refer to Example I for methods and materials.

The effects of cisplatin on inducing apoptosis in T98G glioblastoma cells were tested. DNA damage was measured by PCR™ of a 2.7 Kbp region of the HPRT gene and compared with an internal control region of 150 bp, that is too small to show significant effects of DNA damage. The data is represented as the percentage of the control PCR™ signal. DNA damage was measured in T98G parental cells at zero and six hours after treatment for 1.5 hours with varying concentrations of cisplatin (FIG. 3A.). The results show considerable DNA damage immediately after cisplatin treatment but after time for repair (6 hours), the level of DNA damage is partially reduced.

Figure 3B:
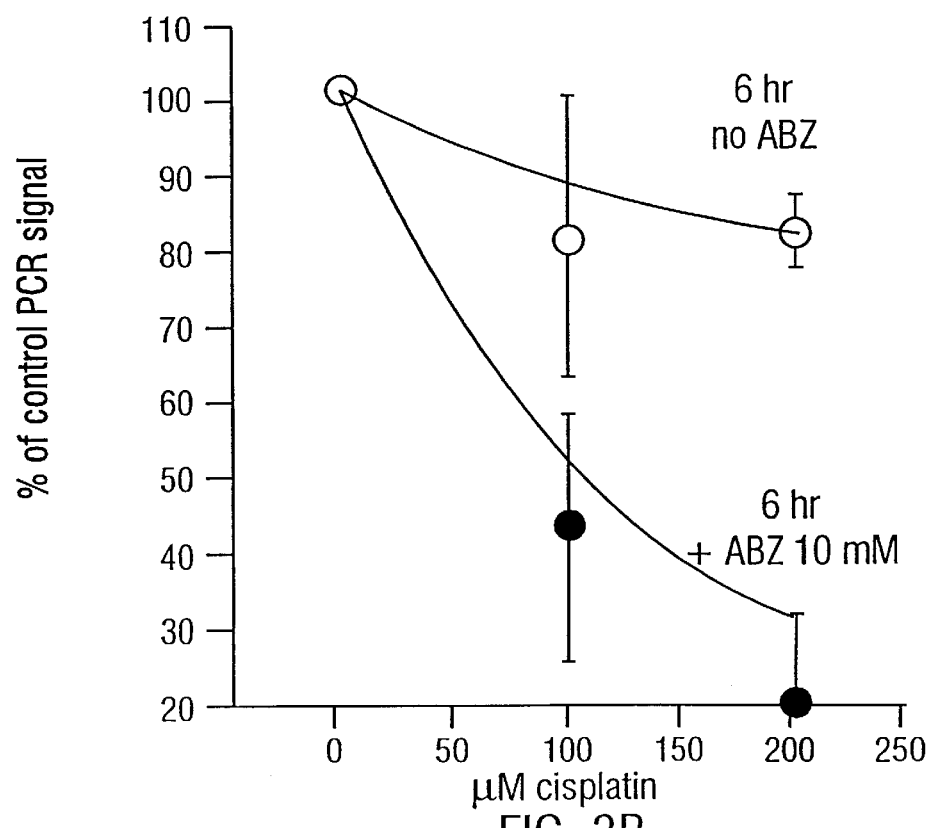
FIG. 3B. DNA damage assay of cisplatin-treated T98G parental cells in the presence (closed circles) or absence (open circles) of 10 mM 3-aminobenzamide. DNA damage was measured 6 hours after a 1.5 hour treatment with cisplatin. DNA damage was measured by PCR™ of a 2.7 Kbp region of the HPRT gene and expressed as the percentage of signal observed after PCR™ of a 150 base pair internal control region. Refer to Example I for methods and materials.

Treatment of T98G parental glioblastoma cells with 10 mM 3-aminobenzamide, an inhibitor of the DNA repair enzyme poly-ADP ribose polymerase and subsequent treatment with varying concentrations of cisplatin resulted in significant DNA damage after six hours post cisplatin treatment (FIG. 3B). In the absence of 3-aminobenzainide no significant DNA damage remained after six hours post-cisplatin treatment. Thus chemical inhibition of a DNA repair mechanism sensitizes T98G tumor cells to apoptosis induced by DNA damaging agents.

Figure 3C:
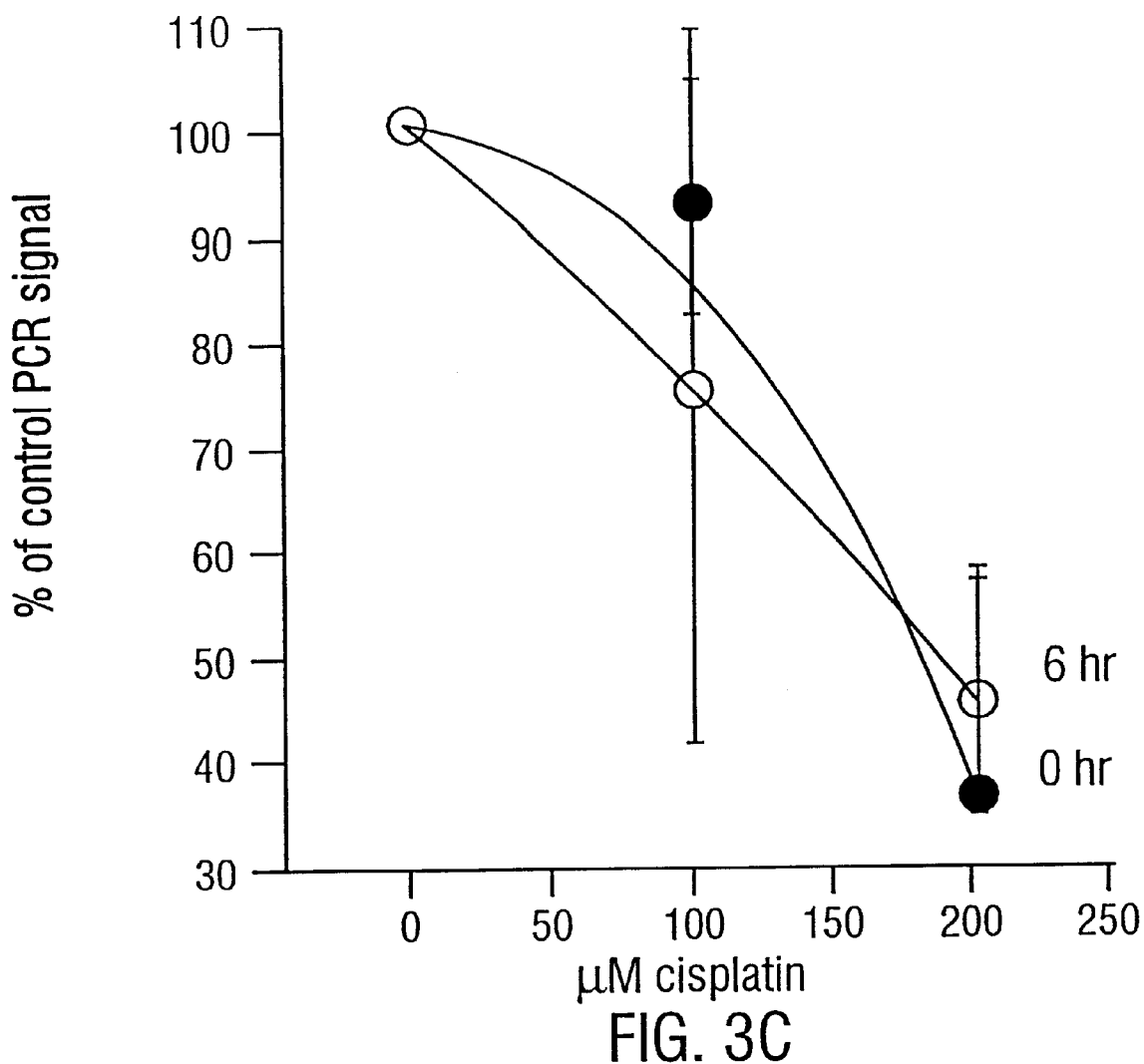
FIG. 3C. DNA damage assay of cisplatin treated T98G-mutant jun cells. DNA damage after zero (closed circles) and six (open circle) hours after a 1.5 hour cisplatin treatment was measured by PCR™ of a 2.7 Kbp region of the HPRT gene and expressed as the percentage of signal observed after PCR™ of a 150 base pair internal control region. Refer to Example I for methods and materials.

T98G-mutant jun cells were exposed to varying concentrations of cisplatin for 1.5 hours and DNA damage was measured at zero and 6 hours post-cisplatin treatment (FIG. 3C). Expression of the mutant jun, which contains two non-phosphorylatable alanine substitutions at critical sites for induction of DNA repair, induced high levels of DNA damage immediately after cisplatin treatment (zero hour) which was not able to be repaired even after six hours. Thus the inhibition of DNA repair at the transcriptional level through blockage of DNA damage-induced AP-1 activity significantly sensitizes tumor cells for progression to apoptosis.

Figure 7A:
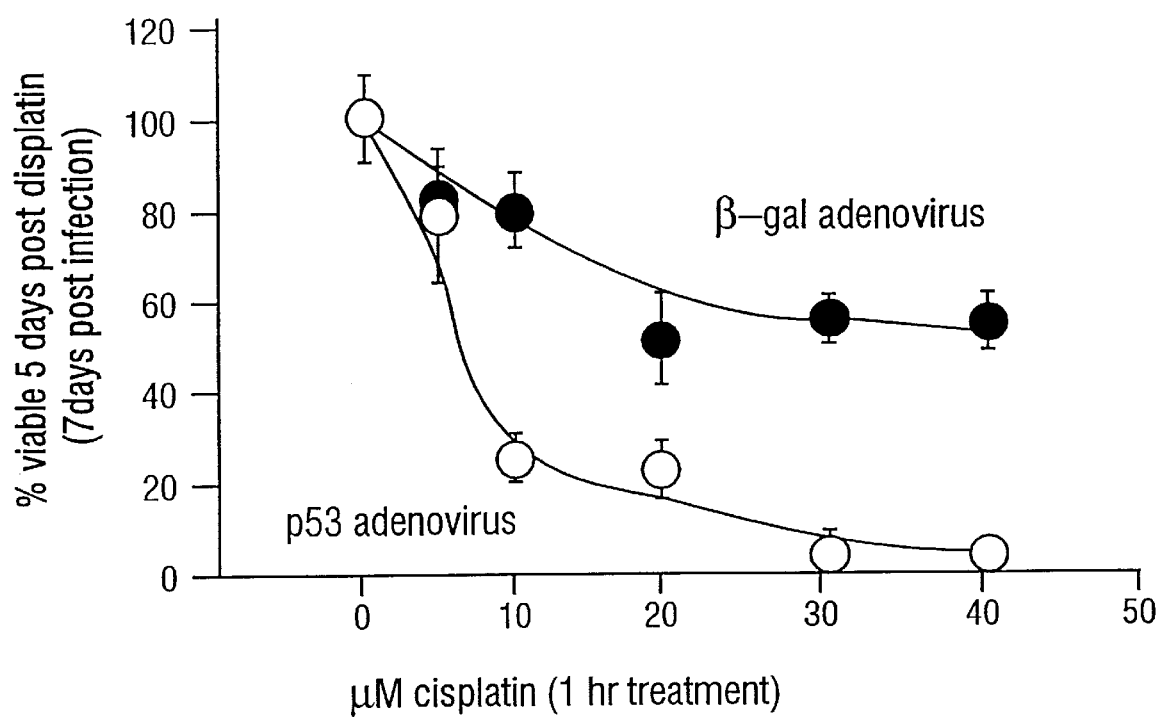
FIG. 7A. Cell growth of T47D breast cancer cells after infection with β-gal adenovirus (closed circles) or p53 adenovirus (open circles) and one hour treatment with various concentrations of cisplatin two days after infection. Cell viability was measured 7 days post-infection. Refer to Example I for methods and materials.
Figure 7B:
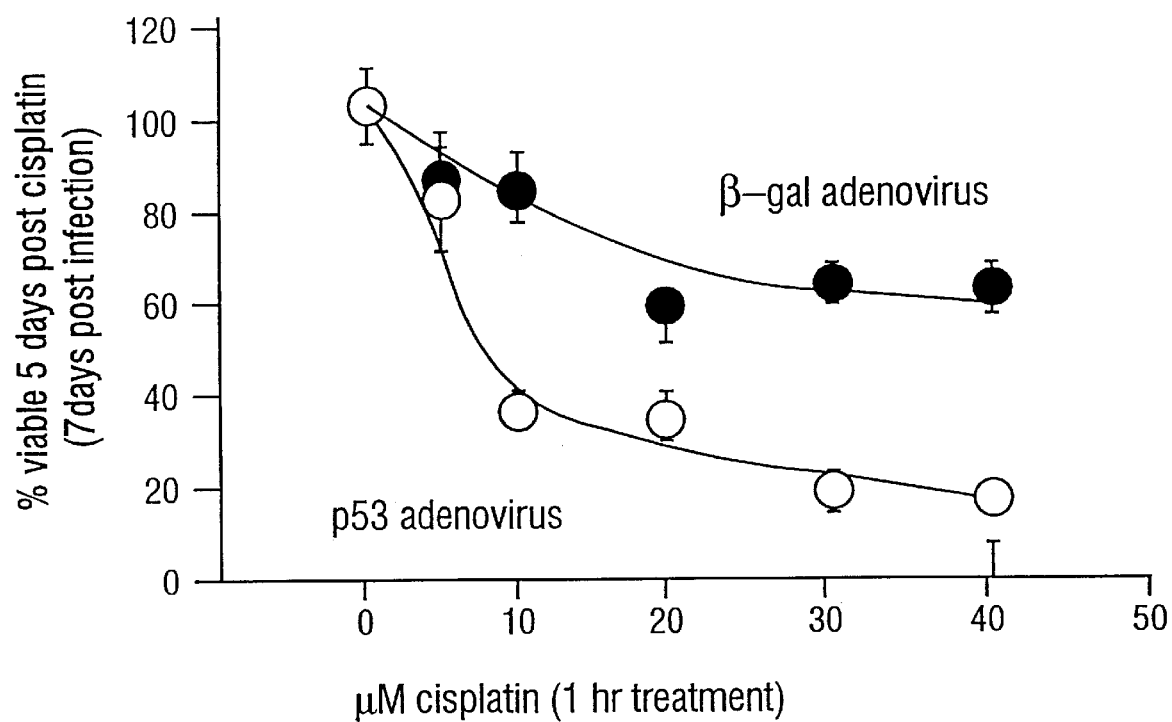
FIG. 7B. Cell growth of T98G glioblastoma cells after infection with β-gal adenovirus (closed circles) or p53 adenovirus (open circles) and one hour treatment with various concentrations of cisplatin two days after infection. Cell viability was measured 7 days post-infection. Refer to Example I for methods and materials.

EXAMPLE V p53-Mediated Tumor Suppression is Enhanced by Increasing Levels of Cisplatin Treatment The effects of increasing levels of cisplatin on the growth characteristics of the following tumor cells were tested: T47D breast carcinoma, T98G glioblastoma, and 9L rat glioblastoma. Cell viability was measured in T47D breast carcinoma cells after infection with wild-type p53 adenovirus and subsequent treatment with cisplatin two days post-infection (FIG. 7A). Cell viability decreased with increasing doses of cisplatin whereas control T47D breast carcinoma cells infected with βgal-adenovirus were significantly more refractory to the DNA damaging effects of cisplatin. Similarly, cisplatin treatment of T98G glioblastoma cells infected with wild-type p53 adenovilLis sensitized the tumor cells to growth suppression in a dose dependent manner (FIG. 7B). T98G glioblastoma cells infected with βgal adenovirus exhibited a slightly reduce growth rate in response to increasing levels of cisplatin.

Figure 7C:
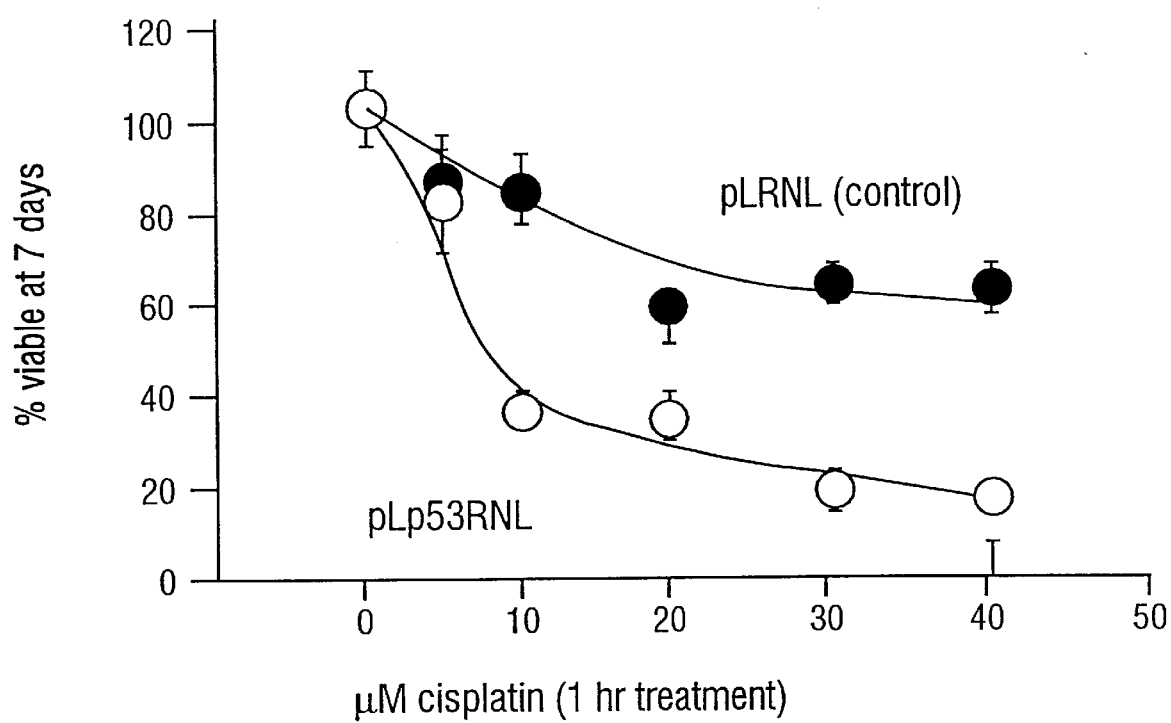
FIG. 7C. Cell growth of T98G glioblastoma cells stably modified with vector only (pLRNL, closed circles) or vector expressing human wild-type p53 (pLp53RNL, open circles) and one hour treatment with various concentrations of cisplatin. Cell viability was measured 7 days post-treatment. Refer to Example I for methods and materials.
Figure 7D:
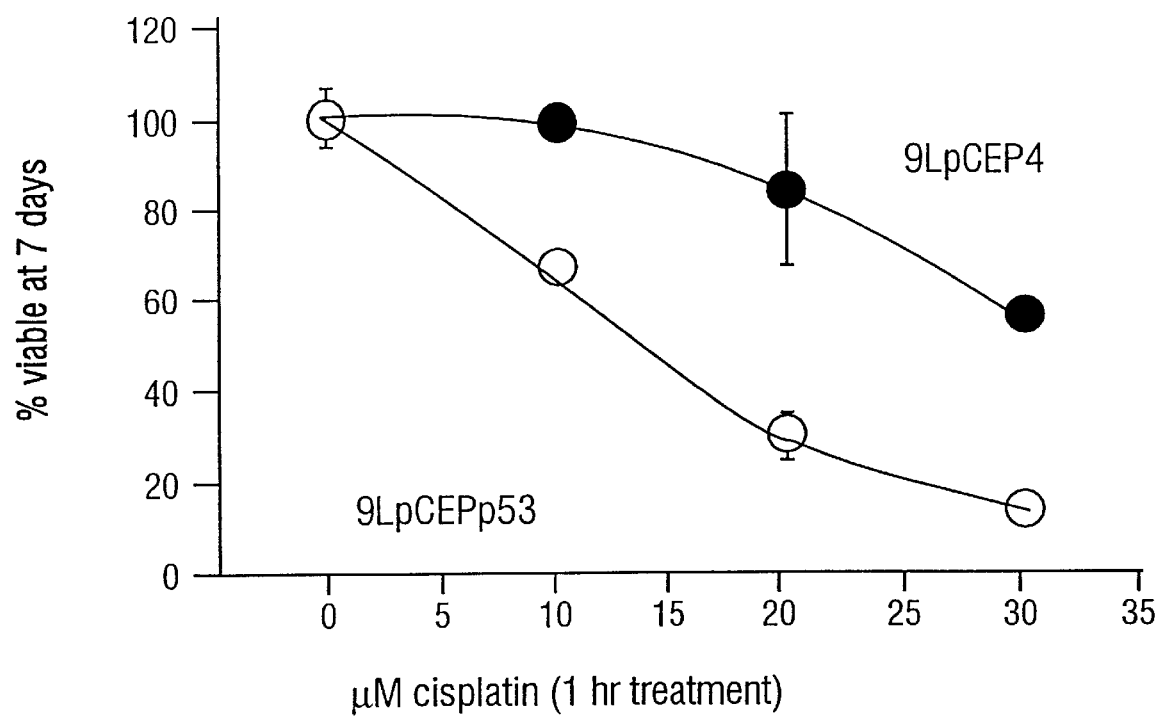
FIG. 7D. Cell growth of 9L rat glioblastoma cells stably modified with vector only (9LpCEP4, closed circles) or vector expressing human wild-type p53 (9LpCEPp53, open circles) and one hour treatment with various concentrations of cisplatin. Cell viability was measured 7 days post-treatment. Refer to Example I for methods and materials.

Tumor cells stably modified with constructs expressing wild-type p53 were also sensitized to the effects of cisplatin. Cell viability of T98G glioblastoma cells stably modified with a vector containing wild-type p53, pLp53RNL was reduced in a dose dependent manner after treatment with increasing doses of cisplatin (FIG. 7C.) Control T98G glioblastoma cells stably modified with vector only, pLNRL, were more resistant to the effects of cisplatin treatment. Similarly, cisplatin treatment of 9L rat glioblastoma cells stably modified by a vector containing wild-type p53, pCEPp53, significantly reduced the viability of the tumor cells in a dose dependent manner as compared to 9L glioblastoma cells stably modified with the control vector pCEP4 (FIG. 7D.). In general then, as cisplatin-induced DNA damage increases, tumor cell growth suppression mediated by p53 concomitantly increases.

I. REFERENCES

The following references, to the extent that they provide exemplary procedural or other details supplementary to those set forth herein, are specifically incorporated herein by reference.

EPO Patent Application No. 0 273 085

Abbondanzo et al., *Breast Cancer Res. Treat.*, 16:182(#151), 1990.

Allred et al., *Breast Cancer Res. Treat.*, 16:182(#149), 1990.

Anderson et al. U.S. Pat. No. 5,399,346, Mar. 12, 1995.

Ausubel et al., In: *Short Protocols in Molecular Biology*, (2nd Ed.), John Wiley and Sons (Eds.), N.Y., 1992.

Baichwal and Sugden, "Vectors for gene transfer derived from animal DNA viruses: Transient and stable expression of transferred genes," In: *Gene Transfer*, Kucherlapati R, Ed., New York, Plenum Press, pp. 117–148, 1986.

Baker et al., "Suppression of human colorectal carcinoma cell growth by wild-type p53," *Science*, 249:912–915, 1990.

Benvenisty and Neshif, "Direction introduction of genes into rats and expression of the genes," *Proc. Nat. Acad. Sci. USA*, 83:9551–9555, 1986.

Bigner et al, "Heterogeneity of genotypic and phenotypic characteristics of fifteen permanent cell lines derived form human glioblastomas," *J. Nveuropath. And Exp. Neurol.*, 40:201–209, 1981.

Bigner et al., "Cytogenetics of human brain tumors," *Cancer Genet. Cytogenet.*, 47:141–154, 1990.

Boussif et al., "A versatile vector for gene and oligonucleotide transfer into cells in culture and in vivo: Polyethylenimine," *Proc. Natl. Acad. Sci. USA*, 92:7297–7301, 1995.

Brown et al., *Breast Cancer Res. Treat.*, 16:192(#191), 1990.

Casey, et al, "Growth suppression of human breast cancer cells by the introduction of a wild-type p53 gene". *Oncogene*, 6:1791–1797, 1991.

Chang el al., "Foreign gene delivery and expression in hepatocytes using a hepatitis B virus vector," *Hepatology*, 14:124A, 1991.

Chen and Okayama, "High-efficiency transfection of mammalian cells by plasmid DNA," *Mol. Cell Biol.*, 7:2745–2752, 1987.

Clarke et al., "Thymocyte apoptosis induced by p53-dependent and independent pathways," *Nature*, 362:849–852, 1993.

Coffin, "Retroviridae and their replication," In: *Virology*, Fields B N, Knipe D M, Ed., New York, Raven Press, pp. 1437–1500, 1990.

Coupar et al, "A general method for the construction of recombinant vaccinia virus expressing multiple foreign genes," *Gene*, 68:1–10, 1988.

Culver et al., "In vivo gene transfer with retroviral vector-producer cells for treatment of experimental brain tumors," *Science*, 256:1550–1552, 1992.

Dannenerg and Saga, In: *Methods for Studying Mononuclear Phagocytes*, Academic Press, New York, N.Y., 375–396, 1981.

Din et al., *J. Biol Chem.*, 267:12804:12812, 1992.

Dubensky et al., "Direct transfection of viral and plasmid DNA into the liver or spleen of mice," *Proc. Nat. Acad. Sci. USA*, 81:7529–7533, 1984.

El-Deiry et al., "WAF1, a potential mediator of p53 tumor suppression," *Cell*, 75:817–825, 1993.

Fanjul et al., "A new class of retinoids with selective inhibition of AP-1 inhibitis proliferation," *Nature*, 372:107–111, 1994.

Fechheimer et al., "Transfection of mammalian cells with plasmid DNA by scrape loading and sonication loading," *Proc. Natl. Acad. Sci. USA*, 84:8463–8467, 1987.

Ferkol et al., "Regulation of the phosphoenolpyruvate carboxykinase/human factor IX gene introduced into the livers of adult rats by receptor-mediated gene transfer," *FASEB J.*, 7:1081–1091, 1993.

Fraley et al., "Entrapment of a bacterial plasmid in phospholipid vesicles: Potential for gene transfer," *Proc. Natl. Acad. Sci. USA*, 76:3348–3352, 1979.

Friedmann, "Progress toward human gene therapy," *Science*, 244:1275–1281, 1989.

Fugiwara et al., "Induction of chemosensitivity in human lung cancer cells in vivo by adenovirus-mediated transfer of the wild-type p53 gene," *Cancer Res.*, 54:2287–2291, 1994.

Ghosh and Bachhawat, "Targeting of liposomes to hepatocytes," In: *Liver Diseases, Targeted Diagnosis and Therapy Using Specific Receptors and Ligands*, Wu G, Wu C., Ed., New York, Marcel Dekker, pp. 87–104, 1991.

Gopal, "Gene transfer method for transient gene expression, stable transfection, and cotransfection of suspension cell cultures," *Mol. Cell Biol.*, 5:1188–1190, 1985.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5", *J. Gen. Virol.*, 36:59–72, 1977.

Grunhaus and Horwitz, "Adenovirus as cloning vector," *Seminar in Virology*, 3:237–252, 1992.

Harland and Weintraub, "Translation of mammalian mRNA injected into Xenopus oocytes is specifically inhibited by antisense RNA," *J. Cell Biol.*, 101:1094–1099, 1985.

Hermonat and Muzycska, "Use of adenoassociated virus as a mammalian DNA cloning vector: Transduction of neomycin resistance into mammalian tissue culture cells," *Proc. Nat. Acad. Sci. USA*, 81:6466–6470, 1984.

Hollestein, et al., "p53 mutations in human cancers." *Science* 253:49–53 1991.

Horwich, et al., "Synthesis of liepadnavirus particles that contain replication-defective duck hepatitis B virus genomes in cultured HuH7 cells," *J. Virol.*, 64:642–650, 1990.

Jaffe et al., "Adenovirus-mediated in vivo transfer and expression in normal rat liver," *Nature Genetics* 1:372–378, 1992.

Jannerwein and Eastman, *Nucleic Acids Res.*, 19:6209–6214, 1991.

Kaden et al., *Proc. Natl. Acad. Sci. USA*, 86:2306–2310, 1989.

Kaneda et al., "Increased expression of DNA cointroduced with nuclear protein in adult rat liver," *Science*, 243:375–378, 1989.

Kato et al., "Expression of hepatitis B virus surface antigen in adult rat liver," *J. Biol. Chem.*, 266:3361–3364, 1991.

Kern et al., *Science*, 256:827–830, 1992.

Klein et al., "High-velocity microprojectiles for delivering nucleic acids into living cells," *Nature*, 327:70–73, 1987.

Lane, "p53: guardian of the genome," *Nature*, 358:15–16, 1992.

Lotem and Sachs, "Hematopoictic cells from mice deficient in wild-type p53 are more resistant to induction of apoptosis by some agents," *Blood*, 82:1092–1096, 1993.

Lowe et al., "p53 status and the efficacy of cancer therapy in vivo," *Science*, 266:807–810, 1994.

Lowe, et al., "p53-mediated apoptosis modulates the cytotoxicity of anti-cancer agents," *Cell*, 74:957–967, 1993.

Mann et al, "Construction of a retrovirus packaging mutant and its use to produce helper-free defective retrovirus," *Cell*, 33:153–159, 1983.

Mercer et al., "Negative growth regulation in a glioblastoma tumor line that conditionally expresses human wild-type p53," *Proc. Natl. Acad. Sci. USA*, 87:6166–6170, 1990.

Mercer, "Cell cycle regulation and the p53 tumor suppressor protein," *Critic. Rev. Eukar. Gene Express.* 2:251–263, 1992.

Montenarh, "Biochemical, immunological, and functional aspects of the growth-suppressor/oncoprotein p53," *Crit. Rev. Oncogen*, 3:233–256, 1992.

Mosmann, "Rapid calorimetric assay for cellular growth and survival: application to proliferation and cytotoxicity assay," *J. Immunol. Methods*, 65:55–63, 1983.

Nicolas and Rubenstein, "Retroviral vectors," In: *Vectors: A Survey of Molecular Cloning Vectors and Their Uses*, Rodriguez R L, Denhardt D T, Ed., Stoneham: Butterworth, pp. 493–513, 1988.

Nicolau and Sene, "Liposome-mediated DNA transfer in eukaryotic cells," *Biochim. Biophys. Acta*, 721:185–190, 1982.

Nicolau et al., "Liposomes as carriers for in vivo gene transfer and expression," *Methods Enzymol.*, 149:157–176, 1987.

Oshita and Saijo, *Jpn. J. Cancer Res.*, 85:669–673, 1994.

Paskind et al., "Dependence of moloney murine leukemia virus production on cell growth," *Virology*, 67:242–248, 1975.

Perales et al., "Gene transfer in vivo: Sustained expression and regulation of genes introduced into the liver by receptor-targeted uptake," *Proc. Natl. Acad. Sci.* 91:4086–4090, 1994.

Potter et al, "Enhancer-dependent expression of human k immunoglobulin genes introduced into mouse pre-B lymphocytes by electroporation," *Proc. Nat. Acad. Sci. USA*, 81:7161–7165, 1984.

Remington's Pharmaceutical Sciences, 18th Ed., Mack Publishing, Easton, Pa., 1990.

Ridgeway, "Mammalian expression vectors," In: *Vectors: A Survey of Molecular Cloning Vectors and Their Uses*, Rodriguez R L, Denhardt D T, Ed., Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rogel et al., "p53 cellular tumor antigen: Analysis of mRNA levels in normal adult tissues, embryos and tumors," *Mol. Cell. Biol.*, 5:2851–2855, 1985.

Rosenfeld et al., "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Nat'l Acad. Sci. USA*, 86:9079–9083, 1989.

Rubinstein et al., "Comparison of in vitro anticancer-drug-screening data generated with a tetrazolium assay versus a protein assay against a diverse panel of human tumor cell lines," *J. Natl. Cancer Inst.*, 82:1113–1120, 1990.

Sambrook's Handbook on Molecular Biology, Cold Spring Harbor Press, 1989.

Satoh and Lindahl, Nature, 356:356–358, 1992.

Shaw et al., "Induction of apoptosis by wild-type p53 in a human colon tumor-derived cell line," *Proc. Natl. Acad. Sci. USA*, 89:4495–4499, 1992.

Smeal et al., *Nature*, 354:494–496, 1991.

Stratford-Perricaudet and Perricaudet, "Gene transfer into animals: the promise of adenovirus," In: *Human Gene*

Transfer, O. Cohen-Haguenauer and M. Boiron, Eds., Editions John Libbey Eurotext, France, pp. 51–61, 1991.

Stratford-Perricaudet et al., "Evaluation of the transfer and expression in mice of an enzyme-encoding gene using a human adenovirus vector," *Hum. Gene. Ther.* 1:241–256, 1990.

Takahashi et al., "Wild-type but not mutant p53 suppresses the growth of human lung cancer cells bearing multiple genetic lesions," *Cancer Res.* 52:2340–2342, 1992.

Temin, "Retrovirus vectors for gene transfer: Efficient integration into and expression of exogenous DNA in vertebrate cell genome," In: Gene Transfer, Kucherlapati R, Ed., New York, Plenum Press, pp. 149–188, 1986.

Tisty, "Normal diploid human and rodent cells lack a detectable frequency of gene amplification," *Proc. Natl. Acad. Sci. USA*, 87:3132–3136, 1990.

Tooze "Molecular biology of DNA Tumor viruses", 2nd Ed. Cold Spring Harbor Laboratory, Cold Spring Harbor, N.Y., 1991.

Tur-Kaspa et al., "Use of electroporation to introduce biologically active foreign genes into primary rat hepatocytes," *Mol. Cell Biol.*, 6:716–718, 1986.

Wagner et al., *Science*, 260:1510–1513, 1993.

Weinberg, "Tumor suppressor gene". *Science* 254:1138–1145, 1991.

Wills et al., *Human Gene Therapy*, 5:1079–1088, 1994.

Wong et al., "Appearance of b-lactamase activity in animal cells upon liposome mediated gene transfer," *Gene*, 10:87–94, 1980.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Yang et al., "In vivo and in vitro gene transfer to mammalian somatic cells by particle bombardment," *Proc. Natl. Acad. Sci. USA*, 87:9568–9572, 1990.

Yonish-Rouach et al., "Wild-type p53 induces apoptosis of myeloid leukemic cells that is inhibited by interleukin-6," *Nature*, 352:345–347, 1991.

Zelenin et al, "High-velocity mechanical DNA transfer of the chloramphenicol acetyltransferase gene into rodent liver, kidney and mammary gland cells in organ explants and in vivo," *FEBS Lett.*, 280:94–96, 1991.

What is claimed is:

1. A method for the induction of p53-mediated apoptosis in a cell comprising (a) determining that said cell expresses a wild-type p53 and (b) contacting said cell with at least one agent that inhibits DNA repair.

2. The method of claim 1, wherein said inhibitory agent inhibits the function of a protein selected from the group consisting of c-jun, c-fos, poly-ADP ribose polymerase, DNA polymerase β, topoisomerase I, d-TMP synthase, hMTII-A, uracil DNA glycosylase, alkyl-N-purine DNA glycosylase, DNA ligase IV, DNA ligase III, Hap-1, Ref-1, poly-ADP ribose polymerase and DNA-dependent protein kinase.

3. The method of claim 2, wherein said inhibitory agent is 3-aminobenzamide.

4. The method of claim 1, further comprising the step of providing to said cell a DNA-damaging agent.

5. The method of claim 4, wherein said DNA-damaging agent is selected from the group consisting of cisplatin, carboplatin, VP16, teniposide, daunorubicin, doxorubicin, dactinomycin, mitomycin, plicamycin, bleomycin, procarbazine, nitrosourea, cyclophosphamide, bisulfan, melphalan, chlorambucil, ifosfamide, merchlorehtamine, taxol, taxotere, anthracyclines and ionizing radiation.

6. The method of claim 1, wherein said cell is a tumor cell.

7. The method of claim 6, wherein said tumor cell is selected from the group consisting of lung tumor cell, a prostate tumor cell, a breast tumor cell, a colon tumor cell, a liver tumor cell, a brain tumor cell, a kidney tumor cell, a skin tumor cell and an ovarian tumor cell.

8. The method claim 6, wherein said tumor cell is selected from the group consisting of a squamous cell carcinoma, a non-squamous cell carcinoma, a glioblastoma, a sarcoma, a melanoma, a papilloma, a neuroblastoma and a leukemia cell.

9. The method of claim 1, wherein said determining comprises an immunoassay.

10. The method of claim 9, wherein said immunoassay comprises immunohistochemistry.

11. The method of claim 9, wherein said immiiunoassay is an ELISA.

12. The method of claim 9, wherein said immunoassay is a Western blot.

13. The method of claim 1, wherein said determining comprises SSCP.

14. The method of claim 1, wherein said determining comprises PCR™.

15. The method of claim 1, wherein said determining comprises sequencing.

16. A method for the induction of p53-mediated apoptosis in a subject comprising administering to said subject at least one agent that inhibits DNA repair.

17. The method of claim 16, wherein said subject is human.

18. The method of claim 17, wherein said inhibitory agent is administered to a tumor site by direct intratumoral injection.

19. The method of claim 18, wherein said injection comprises continuous perfusion.

* * * * *